US009885642B2

(12) United States Patent
Yu

(10) Patent No.: US 9,885,642 B2
(45) Date of Patent: Feb. 6, 2018

(54) DEVICES AND METHODS FOR SEPARATING MAGNETICALLY LABELED MOIETIES IN A SAMPLE

(75) Inventor: Liping Yu, San Jose, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 820 days.

(21) Appl. No.: 13/984,019

(22) PCT Filed: Apr. 5, 2012

(86) PCT No.: PCT/US2012/032423
§ 371 (c)(1),
(2), (4) Date: Aug. 26, 2013

(87) PCT Pub. No.: WO2012/148648
PCT Pub. Date: Nov. 1, 2012

(65) Prior Publication Data
US 2013/0330739 A1     Dec. 12, 2013

Related U.S. Application Data

(60) Provisional application No. 61/479,778, filed on Apr. 27, 2011.

(51) Int. Cl.
*G01N 1/34* (2006.01)
*B03C 1/033* (2006.01)
*B03C 1/035* (2006.01)

(52) U.S. Cl.
CPC .............. *G01N 1/34* (2013.01); *B03C 1/035* (2013.01); *B03C 1/0332* (2013.01); *B03C 2201/18* (2013.01); *B03C 2201/26* (2013.01)

(58) Field of Classification Search
CPC ... B03C 1/0332; B03C 1/035; B03C 2201/18; B03C 2201/26; G01N 1/34
(Continued)

(56) References Cited

U.S. PATENT DOCUMENTS 4,664,796 A    5/1987 Graham et al.
4,769,130 A *  9/1988 Christensen .......... B03C 1/0332
                                                 209/223.1
(Continued)

FOREIGN PATENT DOCUMENTS

JP    1-109263 A    4/1989
JP    8-252723 A    10/1996
(Continued)

OTHER PUBLICATIONS

Iacob et al., "High Gradient Magnetic Separation Ordered Matrices", European Cells and Materials, vol. 3, Suppl. 2, pp. 167-169 (2002).

*Primary Examiner* — Melanie Yu Brown
(74) *Attorney, Agent, or Firm* — Bret E. Field; Bozicevic, Field & Francis LLP

(57) ABSTRACT

Devices for separating magnetically labeled moieties in a sample are provided. Aspects of the devices include a magnetic field source, a first magnetic field guide having a wedge-shaped portion with an apex edge, and a second magnetic field guide having a wedge-shaped portion with an apex edge. The apex edge of the first magnetic field guide is aligned substantially across from and parallel to the apex edge of the second magnetic field guide, and the device is configured to separate magnetically labeled moieties from non-magnetically labeled moieties in the sample. Also provided are methods of using the devices, as well as systems and kits configured for use with the devices and methods.

10 Claims, 11 Drawing Sheets

(58) Field of Classification Search
USPC .................................................. 436/526
See application file for complete search history.

(56) References Cited

U.S. PATENT DOCUMENTS

| | | | |
|---|---|---|---|
| 4,772,383 A | 9/1988 | Christensen | |
| 5,147,562 A | 9/1992 | Heyman | |
| 5,411,863 A | 5/1995 | Miltenyi | |
| 5,527,460 A | 6/1996 | Benes et al. | |
| 5,541,072 A | 7/1996 | Cronin et al. | |
| 5,622,831 A | 4/1997 | Liberti et al. | |
| 5,626,767 A | 5/1997 | Kilburn et al. | |
| 5,665,605 A | 9/1997 | Bolex et al. | |
| 5,688,405 A | 11/1997 | Dickinson et al. | |
| 5,688,406 A | 11/1997 | Dickinson et al. | |
| 5,770,388 A | 6/1998 | Vorphal | |
| 5,795,470 A | 8/1998 | Liberti et al. | |
| 5,837,200 A | 11/1998 | Diessel et al. | |
| 5,876,593 A | 3/1999 | Liberti et al. | |
| 5,902,489 A | 5/1999 | Shimuzu et al. | |
| 5,912,182 A | 6/1999 | Bolek et al. | |
| 5,918,272 A | 6/1999 | Caputi et al. | |
| 5,945,281 A | 9/1999 | Prabhu | |
| 5,968,820 A | 10/1999 | Chalmers et al. | |
| 5,976,369 A | 11/1999 | Bischof et al. | |
| 5,979,664 A | 11/1999 | Brodeur et al. | |
| 5,985,153 A | 11/1999 | Dolan et al. | |
| 6,013,188 A | 1/2000 | Liberti et al. | |
| 6,013,532 A | 1/2000 | Liberti et al. | |
| 6,036,027 A | 3/2000 | Grimes | |
| 6,120,735 A | 9/2000 | Chalmers et al. | |
| 6,126,835 A | 10/2000 | Barbera-Guillem et al. | |
| 6,136,182 A | 10/2000 | Dolan et al. | |
| 6,216,538 B1 | 4/2001 | Yasuda et al. | |
| 6,241,894 B1 | 6/2001 | Briggs et al. | |
| 6,254,830 B1 | 7/2001 | Pivarnik et al. | |
| 6,273,262 B1 | 8/2001 | Yasuda et al. | |
| 6,280,618 B2 | 8/2001 | Watkins et al. | |
| 6,297,061 B1 | 10/2001 | Wu et al. | |
| 6,332,541 B1 | 12/2001 | Coakley et al. | |
| 6,361,749 B1 | 3/2002 | Terstappen et al. | |
| 6,432,630 B1 | 8/2002 | Blankenstein | |
| 6,467,350 B1 | 10/2002 | Kaduchak et al. | |
| 6,467,630 B1 | 10/2002 | Zborowski et al. | |
| 6,613,525 B2 | 9/2003 | Nelson et al. | |
| 6,623,982 B1 | 9/2003 | Liberti et al. | |
| 6,630,355 B1 | 10/2003 | Pivarnik et al. | |
| 6,644,118 B2 | 11/2003 | Kaduchak et al. | |
| 6,645,777 B1 | 11/2003 | Letcher et al. | |
| 6,660,159 B1 | 12/2003 | Terstappen et al. | |
| 6,699,711 B1 | 3/2004 | Hahn et al. | |
| 6,749,666 B2 | 6/2004 | Meegan | |
| 6,790,366 B2 | 9/2004 | Terstappen et al. | |
| 6,797,514 B2 | 9/2004 | Berenson et al. | |
| 6,809,315 B2 | 10/2004 | Ellson et al. | |
| 6,854,338 B2 | 2/2005 | Khuri-Yakub et al. | |
| 6,858,440 B1 | 2/2005 | Letcher et al. | |
| 6,890,426 B2 | 5/2005 | Terstappen et al. | |
| 6,929,750 B2 | 8/2005 | Laurell et al. | |
| 6,932,097 B2 | 8/2005 | Ellson et al. | |
| 7,022,505 B2 | 4/2006 | Chandler et al. | |
| 7,033,473 B2 | 4/2006 | Gascoyne et al. | |
| 7,056,657 B2 | 6/2006 | Terstappen et al. | |
| 7,108,137 B2 | 9/2006 | Lal et al. | |
| 7,138,269 B2 | 11/2006 | Blankenstein | |
| 7,150,779 B2 | 12/2006 | Meegan | |
| 7,232,691 B2 | 6/2007 | Kraus et al. | |
| 7,340,957 B2 | 3/2008 | Kaduchak et al. | |
| 7,373,805 B2 | 5/2008 | Hawkes et al. | |
| 7,474,184 B1* | 1/2009 | Humphries | B03C 1/002 335/296 |
| 7,484,414 B2 | 2/2009 | Priev et al. | |
| 7,521,023 B2 | 4/2009 | Laugharn et al. | |
| 7,666,308 B2 | 2/2010 | Scholtens et al. | |
| 7,670,558 B2 | 3/2010 | Katou et al. | |
| 7,674,630 B2 | 3/2010 | Siversson | |
| 7,722,815 B2 | 5/2010 | Katou et al. | |
| 7,807,454 B2 | 10/2010 | Oh et al. | |
| 7,837,040 B2 | 11/2010 | Ward et al. | |
| 7,846,382 B2 | 12/2010 | Strand et al. | |
| 7,980,752 B2 | 7/2011 | Sarvazyan et al. | |
| 7,998,696 B2 | 8/2011 | Zaugg et al. | |
| 8,071,054 B2 | 12/2011 | Oh et al. | |
| 8,071,395 B2 | 12/2011 | Davis et al. | |
| 8,083,068 B2 | 12/2011 | Kaduchack et al. | |
| 8,134,705 B2 | 3/2012 | Ward et al. | |
| 8,166,819 B2 | 5/2012 | Wanis et al. | |
| 8,227,257 B2 | 7/2012 | Ward et al. | |
| 8,263,387 B2 | 9/2012 | Pagano et al. | |
| 8,263,407 B2 | 9/2012 | Goddard et al. | |
| 8,266,950 B2 | 9/2012 | Kaduchak et al. | |
| 8,266,951 B2 | 9/2012 | Kaduchak et al. | |
| 8,277,764 B2 | 10/2012 | Gilbert et al. | |
| 8,292,083 B2 | 10/2012 | Varghese et al. | |
| 8,300,303 B1 | 10/2012 | Ruffa | |
| 8,309,408 B2 | 11/2012 | Ward et al. | |
| 8,323,568 B2 | 12/2012 | McBrady et al. | |
| 8,372,590 B2 | 2/2013 | Bernard et al. | |
| 8,409,415 B2 | 4/2013 | Liu et al. | |
| 8,436,993 B2 | 5/2013 | Kaduchak et al. | |
| 2006/0038648 A1* | 2/2006 | Humphries | B03C 1/0332 335/306 |
| 2006/0226924 A1 | 10/2006 | Chen et al. | |
| 2007/0182517 A1* | 8/2007 | Humphries | H01F 7/0252 335/306 |
| 2009/0243594 A1* | 10/2009 | Kahlman | B82Y 25/00 324/202 |

FOREIGN PATENT DOCUMENTS

| | | |
|---|---|---|
| JP | 2002-86015 A | 3/2002 |
| JP | 2004-99584 A | 4/2004 |
| JP | 2006-218442 A | 8/2006 |
| JP | 2006-341202 A | 12/2006 |
| WO | WO 2008/010111 A2 | 1/2008 |
| WO | 2009/022994 A1 | 2/2009 |

* cited by examiner

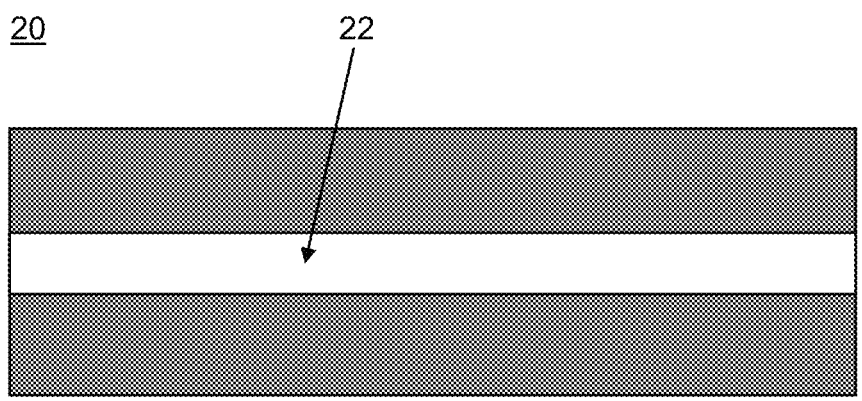
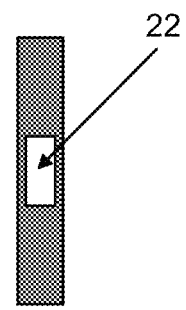
FIG. 2(a)          FIG. 2(b)

FIG. 6(a)
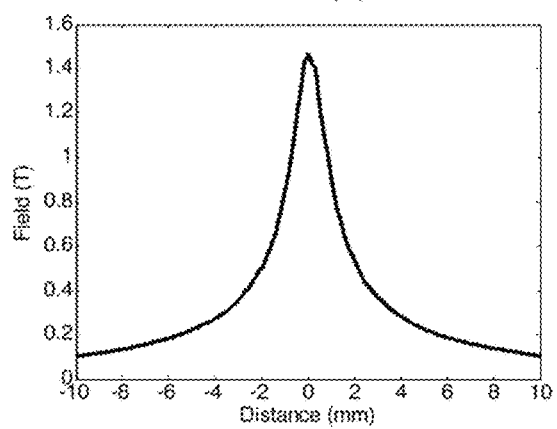
FIG. 6(b)
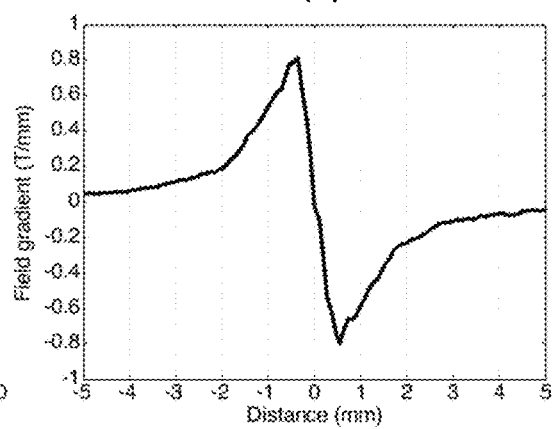
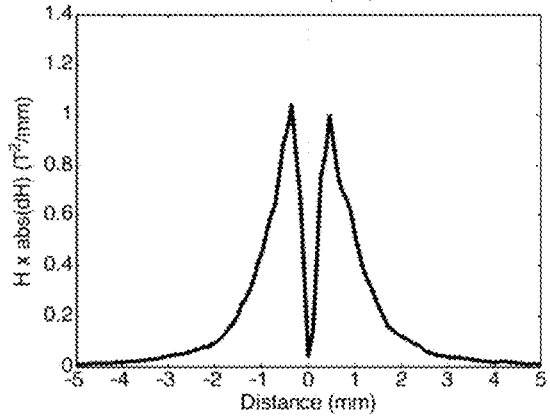
FIG. 6(c)

DEVICES AND METHODS FOR SEPARATING MAGNETICALLY LABELED MOIETIES IN A SAMPLE

CROSS-REFERENCE TO RELATED APPLICATIONS

Pursuant to 35 U.S.C. § 119 (e) this application claims priority to the filing date of U.S. Provisional Patent Application Ser. No. 61/479,778 filed Apr. 27, 2011, the disclosure of which application is herein incorporated by reference.

INTRODUCTION

Magnetic immunoassays have been described in which analyte-specific antibodies conjugated to magnetic particles are used to magnetically label a target analyte to facilitate magnetic separation of the analyte from the sample solution. Typically, after the magnetically labeled analyte has been concentrated against the side or bottom of the sample chamber, the sample fluid is removed. Such assays require sample handling fluidics to separate the captured analyte from the sample fluid and are inherently multi-step.

U.S. Pat. No. 5,945,281 describes a magnetic immunoassay in which a labeled target analyte is magnetically separated from a sample fluid and moved from a sample chamber into a detection region for optical analysis. The sample is added to the sample chamber containing magnetic capture reagents and a label, such that the target analyte in the sample forms a complex with the magnetic capture agent and the label. An electrical potential is applied to the complex to transport the complex to a detection region, and the presence of the complex in the detection region is determined.

U.S. Pat. Nos. 6,858,440; 6,645,777; 6,630,355; and 6,254,830, each incorporated herein by reference, describe a magnetic focusing immunosensor for magnetically concentrating pathogenic bacteria in a food sample onto the side of a sample container and optically detecting the concentrated cells through the side of the sample container. The magnetic focusing immunosensor includes a focusing magnet and fiber optics attached to the side of the magnet for transmitting excitation and detection light.

SUMMARY

Devices and methods for separating magnetically labeled moieties in a sample are provided. Embodiments of the device include magnetic field guides disposed on one or more magnetic field sources, where the magnetic field guides each have a wedge-shaped portion with an apex edge. The apex edges of the magnetic field guides are aligned substantially across from and parallel to each other. In certain cases, the device includes a conduit for carrying a sample flow in close proximity to the apex edges of the magnetic field guides, such that the sample flow is substantially parallel to the apex edges of the magnetic field guides.

Embodiments of the present disclosure may achieve high efficiency, high flow rate and low cost magnetic separation of magnetically labeled moieties in a sample. For example, embodiments of the present disclosure may be used to separate cells and other molecules that are labeled with magnetic particles from a biological fluid sample. In some instances, the efficiency of separation of the magnetically labeled moieties from the sample depends on the magnetic field and the magnetic field gradient produced by the magnetic field source. In some cases, the force on the magnetic labels, and thus the efficiency of magnetic separation, depends on the product of the magnetic field and the magnetic field gradient. Thus, embodiments of the present disclosure may achieve both a high magnetic field and high magnetic field gradient in the same spatial location, e.g., in the area between and/or proximal to the apex edges of the magnetic field guides through which the sample flows. The high magnetic field and high magnetic field gradient produced by the device may increase the separation efficiency of the device, and thus allow for increased sample flow rates through the device for high throughput separation.

In certain embodiments, the device is configured to separate magnetically labeled moieties from non-magnetically labeled moieties in a sample that flows through the device. In some cases, the device includes a magnetic field source, such as a single magnetic field source. In other cases, the device includes a first magnetic field source and a second magnetic field source, which may be arranged on opposite sides of a fluid conduit. In some instances, the magnetic field source may be a permanent magnet, rather than other types of magnets such as an electromagnet. Embodiments of the device that include a permanent magnet as the magnetic field source provide a sustained magnetic field without the need for an external power source, and thus may be less complex and lower in cost to manufacture and operate than a device that includes other types of magnets, such as electromagnets.

The device also includes a first magnetic field guide and a second magnetic field guide. In embodiments of the device that include one magnetic field source, the first and second magnetic field guides may be disposed on opposite sides of the magnetic field source. In other embodiments of the device that include first and second magnetic field sources, the first magnetic field guide may be disposed on a surface of the first magnetic field source facing the second magnetic field source, and the second magnetic field guide that may be disposed on a surface of the second magnetic field source facing the first magnetic field source. The first magnetic field guide and the second magnetic field guide each have a wedge-shaped portion with an apex edge. The first and second magnetic field guides are arranged such that the apex edge of the first magnetic field guide is aligned substantially across from and parallel to the apex edge of the second magnetic field guide. In some instances, the magnetic field guides are soft magnets.

Each magnetic field guide has a wedge-shaped portion and may be configured to direct the magnetic flux from the associated magnetic field source towards the area proximal to the apex edge of the magnetic field guide. In some cases, the wedge-shaped portion of the magnetic field guide focuses the magnetic flux from the interface between the magnetic field source and the magnetic field guide, where the interface has a relatively large cross-sectional area, to the apex edge of the magnetic field guide, which has a relatively small cross-sectional area. The wedge-shaped portion of the magnetic field guide may be configured to focus the magnetic flux from the associated magnetic field source with minimal magnetic flux leakage during the transmission of the magnetic flux through the magnetic field guide. In certain embodiments, the tapered wedge shape portion of the magnetic field guide focuses the magnetic flux from the associated magnetic field source, resulting in an increase in the magnetic flux from the magnetic field source in the area proximal to (e.g., near and/or between) the apex edge of the magnetic field guide. The resulting high magnetic field strength and high magnetic field gradient in the area proximal to (e.g., near and/or between) the apex edge of the magnetic field guide may increase the efficiency of the separation of magnetically labeled moieties from non-labeled moieties in the sample being analyzed.

A fluid conduit for directing the flow of a sample fluid through the device may be positioned in the area between or proximal to the apex edges of the magnetic field guides such that a longitudinal axis of the conduit is substantially parallel to the apex edges of the first and second magnetic field guides. As such, in certain embodiments, the sample fluid is directed by the conduit to flow in close proximity to and substantially parallel to the apex edges of the magnetic field guides. Positioning the conduit in close proximity to and substantially parallel to the apex edges of the magnetic field guides may maximize the amount of time the sample fluid flow is exposed to the locally high magnetic field and magnetic field gradient in the area proximal to the apex edges of the magnetic field guides, and thus may increase the separation efficiency of the device.

As the sample flows through the conduit, magnetically labeled moieties in the sample are retained in the conduit by the magnetic field produced by the device. Non-labeled moieties in the sample are not retained in the conduit and flow through the device. The retained magnetically labeled moieties can be recovered by positioning the conduit away from the magnetic field and flushing the magnetically labeled moieties from the conduit. The conduit may be positioned in the magnetic field and positioned away from the magnetic field either manually or automatically. In some cases, the conduit may be disposable, such as a single-use conduit, which may be suitable for clinical applications.

Aspects of the present disclosure further include systems for separating magnetically labeled moieties in a sample, where the system includes one or more magnetic separation devices as described herein. In certain embodiments, the system includes two magnetic separation devices, such as a first magnetic separation device and a second magnetic separation device arranged downstream from the first magnetic separation device. The apex edges of the first and second magnetic field guides of the first magnetic separation device may have substantially the same profiles as the apex edges of the first and second magnetic field guides of the second magnetic separation device. For example, the apex edges of the first and second magnetic field guides of the first magnetic separation device and the apex edges of the first and second magnetic field guides of the second magnetic separation device may each have a linear profile. In other embodiments, the apex edges of the first and second magnetic field guides of the first magnetic separation device have different profiles from the apex edges of the first and second magnetic field guides of the second magnetic separation device. For instance, the apex edges of the first and second magnetic field guides of the first magnetic separation device may each have a linear profile and the apex edges of the first and second magnetic field guides of the second magnetic separation device may each have a saw-tooth profile.

Accordingly, embodiments of the present disclosure include a device for separating magnetically labeled moieties in a sample. The device includes a magnetic field source, a first magnetic field guide having a wedge-shaped portion with an apex edge, and a second magnetic field guide having a wedge-shaped portion with an apex edge. One or more of the first and second magnetic field guides is configured to increase a magnetic flux from the magnetic field source, the apex edge of the first magnetic field guide is aligned substantially across from and parallel to the apex edge of the second magnetic field guide, and the device is configured to separate magnetically labeled moieties from non-magnetically labeled moieties in the sample.

Embodiments of the device may also include that both the first and second magnetic field guides are configured to increase the magnetic flux from the magnetic field source.

Embodiments of the device may also include that a cross-sectional profile of one of more of the first magnetic field guide and the second magnetic field guide tapers to a point at the apex edge.

Embodiments of the device may also include that one of more of the first magnetic field guide and the second magnetic field guide has a rounded cross-sectional profile at the apex edge.

Embodiments of the device may also include that the apex edge of the first magnetic field guide is a substantially uniform distance along its length from the apex edge of the second magnetic field guide.

Embodiments of the device may also include that the apex edge of the first magnetic field guide is a distance from the apex edge of the second magnetic field guide ranging from 0.1 mm to 5 mm.

Embodiments of the device may also include that the apex edge of the first magnetic field guide and the apex edge of the second magnetic field guide each have a linear profile.

Embodiments of the device may also include that the apex edge of the first magnetic field guide and the apex edge of the second magnetic field guide each have a saw-tooth profile.

Embodiments of the device may also include that the first magnetic field guide and the second magnetic field guide each have an apex angle of 90 degrees or less. Embodiments of the device may also include that the first magnetic field guide and the second magnetic field guide each include a soft magnet.

Embodiments of the device may also include a conduit positioned between the first magnetic field guide and the second magnetic field guide and configured to direct a flow of the sample through the device.

Embodiments of the device may also include that the conduit is positioned such that a longitudinal axis of the conduit is substantially parallel to a longitudinal axis of the first magnetic field guide and a longitudinal axis of the second magnetic field guide.

Embodiments of the device may also include that the first magnetic field guide and the second magnetic field guide are disposed on opposite sides of the magnetic field source.

Embodiments of the device may also include a second magnetic field source.

Embodiments of the device may also include that the first magnetic field guide is disposed on a surface of the magnetic field source facing the second magnetic field guide and is configured to increase the magnetic flux from the magnetic field source, and the second magnetic field guide is disposed on a surface of the second magnetic field source facing the first magnetic field guide and is configured to increase a magnetic flux from the second magnetic field source.

Embodiments of the device may also include that the device is configured to automatically position the conduit in the device.

Embodiments of the device may also include that the conduit has a tapered cross-sectional shape such that the cross-sectional dimension of the conduit proximal to the apex edges of the first and second magnetic field guides is less than the cross-sectional dimension distal to the apex edges of the first and second magnetic field guides.

Embodiments of the device may also include that the conduit is substantially free from magnetic gradient enhancing materials.

Embodiments of the device may also include that the conduit is configured to be positionable away from the magnetic field.

Embodiments of the device may also include that the magnetic field source includes a permanent magnet.

Embodiments of the device may also include that the permanent magnet includes a rare-earth magnet.

In some embodiments, a method of separating magnetically labeled moieties in a sample is provided. The method includes positioning in a magnetic separation device a conduit configured to direct a flow of a sample through the magnetic separation device, and applying a magnetic field to separate magnetically labeled moieties from non-magnetically labeled moieties in the sample. The magnetic separation device includes a magnetic field source, a first magnetic field guide having a wedge-shaped portion with an apex edge, and a second magnetic field guide having a wedge-shaped portion with an apex edge, where one or more of the first and second magnetic field guides is configured to increase a magnetic flux from the magnetic field source, and the apex edge of the first magnetic field guide is proximal to and substantially parallel to the apex edge of the second magnetic field guide.

Embodiments of the method may also include that the positioning includes positioning the conduit in the device such that a longitudinal axis of the conduit is substantially parallel to a longitudinal axis of the first magnetic field guide and a longitudinal axis of the second magnetic field guide.

Embodiments of the method may also include positioning the conduit away from the magnetic field, and recovering the magnetically labeled moieties retained in the conduit.

Embodiments of the method may also include that the positioning the conduit away from the magnetic field includes removing the conduit from the device.

Embodiments of the method may also include that the positioning the conduit away from the magnetic field includes moving the magnetic field source away from the conduit.

Embodiments of the method may also include that the recovering includes flushing the magnetically labeled moieties from the conduit.

Embodiments of the method may also include specifically attaching a magnetic label to target moieties in the sample prior to applying the magnetic field to the sample.

Embodiments of the method may also include that the sample includes a biological sample.

In some embodiments, a system for separating magnetically labeled moieties in a sample is provided. The system includes one or more magnetic separation devices for separating magnetically labeled moieties in the sample, where each of the one or more magnetic separation devices includes a magnetic field source, a first magnetic field guide having a wedge-shaped portion with an apex edge, and a second magnetic field guide having a wedge-shaped portion with an apex edge. One or more of the first and second magnetic field guides is configured to increase a magnetic flux from the magnetic field source, the apex edge of the first magnetic field guide is proximal to and substantially parallel to the apex edge of the second magnetic field guide, and the device is configured to separate magnetically labeled moieties from non-magnetically labeled moieties in the sample. The system also includes a conduit positioned in the magnetic separation device and configured to direct a flow of the sample through the magnetic separation device.

Embodiments of the system may also include that the conduit is positioned such that a longitudinal axis of the conduit is substantially parallel to a longitudinal axis of the first magnetic field guide and a longitudinal axis of the second magnetic field guide.

Embodiments of the system may also include that the system includes one magnetic separation device.

Embodiments of the system may also include that the system includes a first magnetic separation device and a second magnetic separation device arranged downstream from the first magnetic separation device.

Embodiments of the system may also include that the apex edges of the first and second magnetic field guides of the first magnetic separation device have substantially the same profiles as the apex edges of the first and second magnetic field guides of the second magnetic separation device.

Embodiments of the system may also include that the apex edges of the first and second magnetic field guides of the first magnetic separation device and the apex edges of the first and second magnetic field guides of the second magnetic separation device each have a linear profile.

Embodiments of the system may also include that the apex edges of the first and second magnetic field guides of the first magnetic separation device have different profiles from the apex edges of the first and second magnetic field guides of the second magnetic separation device.

Embodiments of the system may also include that the apex edges of the first and second magnetic field guides of the first magnetic separation device each have a linear profile and the apex edges of the first and second magnetic field guides of the second magnetic separation device each have a saw-tooth profile.

Embodiments of the system may also include a flow cytometer arranged downstream from the one or more magnetic separation devices.

BRIEF DESCRIPTION OF THE FIGURES

FIG. 2(a) shows a schematic of a longitudinal cross section of a conduit, according to embodiments of the present disclosure. FIG. 2(b) shows a schematic of a front view of a conduit, according to embodiments of the present disclosure.

FIGS. 6(a), 6(b) and 6(c) show graphs of a simulated magnetic field (FIG. 6(a)), magnetic field gradient (FIG. 6(b)), and product of the magnetic field and absolute magnetic field gradient (FIG. 6(c)) across the gap between the magnetic field guides as shown in FIG. 1(a) for a magnetic separation device with a distance between the apex edges of the magnetic field guides of 1.4 mm, according to embodiments of the present disclosure. The x-axis is along the center of the gap from left to right between the apex edges of the magnetic field guides, as shown in FIG. 3(a).

DETAILED DESCRIPTION

Figure 1A:
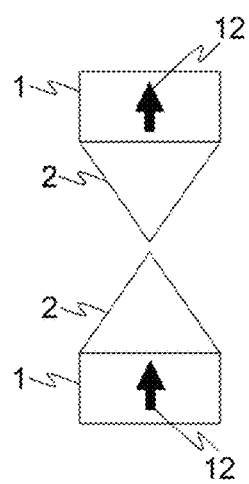
FIG. 1(a) shows a schematic of a front view of a magnetic separation device that includes two magnetic field sources, according to embodiments of the present disclosure.

Devices for separating magnetically labeled moieties in a sample are provided. Aspects of the devices include a magnetic field source, a first magnetic field guide having a wedge-shaped portion with an apex edge, and a second magnetic field guide having a wedge-shaped portion with an apex edge. The apex edge of the first magnetic field guide is aligned substantially across from and parallel to the apex edge of the second magnetic field guide, and the device is configured to separate magnetically labeled moieties from non-magnetically labeled moieties in the sample. Also provided are methods of using the devices, as well as systems and kits configured for use with the devices and methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the present disclosure, aspects of embodiments of the devices will be described first in greater detail. Next, embodiments of methods, systems and kits that may be used with the devices are reviewed.

Devices

Provided are devices for separating magnetically labeled moieties in a sample. The device may be configured to separate magnetically labeled moieties from non-magnetically labeled moieties (e.g., moieties that are not associated with a magnetic label) in the sample. In certain instances, the device separates magnetically labeled moieties of interest from moieties that are not of interest (e.g., moieties that are not magnetically labeled) by retaining the magnetically labeled moieties in the device while not retaining moieties that are not of interest. Because the moieties of interest are magnetically labeled, the device may be configured to retain the magnetically labeled moieties in the device by attracting the magnetically labeled moieties to a magnetic field source in the device and retaining the magnetically labeled moieties in the device. In other cases, the device separates magnetically labeled moieties that are not of interest from moieties that are of interest (e.g., moieties of interest that are not magnetically labeled) by retaining the magnetically labeled moieties that are not of interest in the device while not retaining moieties that are of interest. In these embodiments, because the moieties of interest are not magnetically labeled, the moieties of interest are not retained in the device and flow through the device. The device may be configured to retain the magnetically labeled moieties that are not of interest in the device by attracting the magnetically labeled moieties to a magnetic field source in the device and retaining the magnetically labeled moieties that are not of interest in the device.

The device may be configured as a flow-through device for analyzing liquid samples. By "flow-through" is meant that a liquid sample may enter the device through an inlet, be carried through the device in a flow path, such as a conduit, and then exit the device through an outlet. The device may be configured to carry a continuous stream of the sample through the device and continuously separate magnetically labeled moieties in the sample as the sample flows through the device. In certain embodiments, the device is configured to have a flow rate of 1 µL/min or more, such as 10 µL/min or more, including 50 µL/min or more, or 100 µL/min or more, or 200 µL/min or more, or 300 µL/min or more, or 400 µL/min or more, or 500 µL/min or more, or 750 µL/min or more, or 1 mL/min or more, or 2 mL/min or more, or 5 mL/min or more, or 10 mL/min or more.

The magnetic separation device may be configured to separate magnetically labeled moieties from a simple sample or complex sample. By "simple sample" is meant a sample that includes one or more magnetically labeled moieties and few, if any, other molecular species apart from the solvent. By "complex sample" is meant a sample that includes the one or more magnetically labeled moieties of interest and also includes many other molecules that are not of interest, such as different proteins, cells, and the like. In certain embodiments, the complex sample is a blood sample, by which is meant blood or a fraction thereof, e.g., serum. In certain embodiments, the complex sample is a serum sample. In certain embodiments, the complex sample assayed using the devices disclosed herein is one that includes 10 or more, such as 20 or more, including 100 or more, e.g., $10^3$ or more, $10^4$ or more (such as 15,000; 20,000 or even 25,000 or more) distinct (i.e., different) molecular entities that differ from each other in terms of molecular structure.

In certain embodiments, the device is configured to separate magnetically labeled moieties from a biological sample. A "biological sample" encompasses a variety of sample types obtained from an organism and can be used in a diagnostic or monitoring assay. For example, a biological sample encompasses blood, blood-derived samples, and other liquid samples of biological origin, solid tissue samples such as a biopsy specimen or tissue cultures or cells derived therefrom and the progeny thereof. A biological sample may also include samples that have been manipulated in any way after their procurement, such as by treatment with reagents, solubilization, enrichment for certain components, or labeling (e.g., labeling with a magnetic label). The term "biological sample" encompasses a clinical sample, and also includes cells in culture, cell supernatants, cell lysates, serum, plasma, cerebrospinal fluid, urine, saliva, biological fluid, and tissue samples.

Moieties of interest may include any moiety that can be stably associated with a magnetic label detectable by the devices disclosed herein. By "stably associated" is meant that the magnetic label and the moiety of interest maintain their position relative to each other in space under the conditions of use, e.g., under the assay conditions. As such, the magnetic label and the moiety of interest can be non-covalently or covalently stably associated with each other. Examples of non-covalent associations include non-specific adsorption, binding based on electrostatic (e.g. ion, ion pair interactions), hydrophobic interactions, hydrogen bonding interactions, specific binding through a specific binding pair member covalently attached to the moiety of interest or the magnetic label, combinations thereof, and the like. Examples of covalent binding include covalent bonds formed between the magnetic label and a functional group present on the moiety of interest, e.g. —OH, where the functional group may be naturally occurring or present as a member of an introduced linking group. Accordingly, the magnetic label may be adsorbed, physisorbed, chemisorbed, or covalently attached to the surface of the moiety of interest.

Magnetic Field Source

Aspects of embodiments of the device for separating magnetically labeled moieties in a sample include one or more magnetic field sources. The magnetic field source may be configured to produce a magnetic field. In certain cases, the magnetic field source produces an inhomogeneous magnetic field. By "inhomogeneous" is meant that the magnetic field has a magnetic field gradient, where the strength of the magnetic field is different depending on the position within the magnetic field. For instance, the magnetic field may have a magnetic field gradient, where the magnetic field strength is greater at one area and gradually decreases at positions further away from that area. Thus, the magnetic field source may be configured to produce a magnetic field having a magnetic field gradient.

In some instances, the device is configured to produce a magnetic field sufficient to separate the magnetically labeled moieties in the sample. The ability of the magnetic field to separate the magnetically labeled moieties in the sample may depend on various parameters, such as the magnetic field strength, the magnetic field gradient, the type of magnetic label, the size of the magnetic label, the distance between the magnetically labeled moieties and the magnetic field source, etc. In certain instances, the force the magnetic field is able to exert on a magnetic label is proportional to the magnetic field strength and the magnetic field gradient. In some cases, the magnetic field source is configured to produce a magnetic field having a magnetic force sufficient to separate magnetically labeled moieties form non-magnetically labeled moieties in the sample. For example, the magnetic field source may be configured to produce a magnetic field having a magnetic field gradient such that the product of the magnetic field and the magnetic field gradient is sufficient to separate magnetically labeled moieties from non-magnetically labeled moieties in the sample.

The magnetic field source may be of any shape that may facilitate the separation of the magnetically labeled moieties from the non-magnetically labeled moieties in the sample. For example, the magnetic field source may be elongated, such that the magnetic field source has a length that is greater than the transverse width of the magnetic field source.

In certain embodiments, the device may be configured to direct a flow of the sample through the device such that the sample flow is proximal to the magnetic field source. Minimizing the distance between the magnetic field source and the sample, and thereby minimizing the distance between the magnetic field source and the magnetically labeled moieties in the sample may facilitate the retention of the magnetically labeled moieties in the device. In some cases, the device is configured to direct the flow of the sample through the device to maximize the length of the flow path that is proximal to the magnetic field source. For example, the device may be configured to direct the flow of the sample through the device such that the sample flow is substantially parallel to the longitudinal axis of the magnetic field source.

In certain embodiments, the device includes one magnetic field source. In some cases, the magnetic field source is configured to produce a magnetic field sufficient to separate magnetically labeled moieties form non-magnetically labeled moieties in the sample. For example, the magnetic field source may be configured to produce a magnetic field sufficient to retain the magnetically labeled moieties in the device. In embodiments that include one magnetic field source, the device may be configured to direct the flow of the sample through the device such that the sample flows through an area near the magnetic field source. In some cases, the device is configured to direct the flow of the sample through the device such that the sample flow is substantially parallel to a longitudinal axis of the magnetic field source. The device may also be configured to direct the flow of the sample through an area near the magnetic field source, where the magnetic field and magnetic field gradient produced by the magnetic field source may be strongest.

In other embodiments, the device includes two magnetic field sources, although the device may include any number of magnetic field sources, such as 2, 3, 4, 5, 6, 7, 8, 9, 10, 15, 20, 25, 30, 35, 40, 45, or 50 or more magnetic field sources as desired. For instance, the device may include a first magnetic field source and a second magnetic field source. In some cases, the first magnetic field source and the second magnetic field source are configured to produce an inhomogeneous magnetic field (e.g., a magnetic field having a magnetic field gradient) sufficient to separate magnetically labeled moieties form non-magnetically labeled moieties in the sample. The first magnetic field source and the second magnetic field source may be configured to produce a magnetic field sufficient to retain the magnetically labeled moieties in the device. In certain embodiments, the first and second magnetic field sources are arranged such that a magnetic field is produced in an area between the magnetic field sources. As such, the first and second magnetic field sources may be configured to produce a magnetic field sufficient to retain the magnetically labeled moieties in an area between the magnetic field sources.

In certain embodiments, the first magnetic field source has a surface that faces the second magnetic field source, and the second magnetic field source has a surface that faces the first magnetic field source, such that these two surfaces are opposing each other. The surface of the first magnetic field source that faces the second magnetic field source may be substantially planar. Similarly, the surface of the second magnetic field source that faces the first magnetic field source may be substantially planar. In some instances, the surfaces of the first magnetic field source and the second magnetic field source that face each other are substantially parallel to each other. In these instances, the opposing surfaces of the first and second magnetic field sources may be a substantially uniform distance from each other. In other embodiments, the opposing surfaces of the first and second magnetic field sources are not parallel to each other, such that one end of the first magnetic field source is closer to the second magnetic field source than the opposite end of the first magnetic field source. In some cases, the first magnetic field source and the second magnetic field source are both elongated. The longitudinal axis of the first magnetic field source may be substantially parallel to the longitudinal axis of the second magnetic field source.

In embodiments that include a first magnetic field source and a second magnetic field source, the magnetization vectors of the first magnetic field source and the second magnetic field source may be aligned in substantially the same direction. In some instances, having a first magnetic field source and a second magnetic field source with magnetization vectors aligned in substantially the same direction facilitates the formation of a magnetic field and a magnetic field gradient in an area between the first and second magnetic field sources. In certain embodiments, the magnetization vector of the first magnetic field source is substantially perpendicular to the surface that faces the second magnetic field source. In some cases, the magnetization vector of the second magnetic field source is substantially perpendicular to the surface that faces the first magnetic field source. In certain instances, the magnetization vectors of the first and second magnetic field sources are both substantially perpendicular to the surfaces of the first and second magnetic field sources that face each other and are aligned in substantially the same direction.

In embodiments that include first and second magnetic field sources, the device may be configured to direct the flow of the sample through the device such that the sample flows through an area between the first magnetic field source and the second magnetic field source. In some cases, as described above, the first and the second magnetic field sources are aligned such that their longitudinal axes are substantially parallel. In these cases, the device may be configured to direct the flow of the sample through the device such that the sample flow is substantially parallel to the longitudinal axes of the first and second magnetic field sources. The device may also be configured to direct the flow of the sample through an area between the first and second magnetic field sources, where the magnetic field and magnetic field gradient produced by the first and second magnetic field sources may be strongest.

The magnetic field source may include a permanent magnet, an electromagnet, a superconducting magnet, combinations thereof, and the like. In certain embodiments, the magnetic field source includes one or more permanent magnets. A "permanent magnet" is a magnetic material that has a persistent magnetic field such that the magnetic field does not substantially decrease over time. In contrast, the term "soft magnet" refers to a material that can be magnetized in the presence of an applied external magnetic field, but whose magnetism substantially decreases when the external magnetic field is removed. In embodiments where the magnetic field source includes one or more permanent magnets, the use of permanent magnets may facilitate the production of a magnetic field without the need for external energy input into the device to power the magnetic field source. In some cases, a permanent magnet costs less than an electromagnet or a superconducting magnet that produces a magnetic field with a substantially similar magnetic field strength and magnetic field gradient. In these cases, the use of a permanent magnet may reduce the cost of the magnetic field source, and thus reduce the overall cost of the device. In certain cases, when the magnetic field source includes one or more permanent magnets, the use of a permanent magnet may facilitate the production of a device that is less complex than a device that includes an electromagnet and/or a superconducting magnet. For example, embodiments of the device that include a permanent magnet may not need to include components associated with an electromagnet and/or a superconducting magnet, such as a power source, electrical circuits associated with the magnetic field source, cooling components associated with the electromagnet and/or superconducting magnet, temperature sensors, and the like.

In some instances, the magnetic field source includes two or more permanent magnets. The permanent magnets may be of any desirable shape, and in some instances may be cube or bar-shaped permanent magnets. In certain cases, the magnetic field source may have a length ranging from 1 cm to 100 cm, such as from 1 cm to 75 cm, including from 1 cm to 50 cm, or from 1 cm to 25 cm, or from 1 cm to 10 cm, or from 5 cm to 10 cm, for example from 5 cm to 6 cm; a width ranging from 0.1 cm to 100 cm, such as from 0.1 cm to 75 cm, including from 0.1 cm to 50 cm, or from 0.1 cm to 25 cm, or form 0.1 cm to 10 cm, or from 0.1 cm to 5 cm, or from 0.1 cm to 2 cm, or from 0.5 cm to 2 cm, for example from 1 cm to 1.5 cm; and a height ranging from 0.1 cm to 100 cm, such as from 0.1 cm to 75 cm, including from 0.1 cm to 50 cm, or from 0.1 cm to 25 cm, or from 0.1 cm to 10 cm, or from 0.1 cm to 5 cm, or from 0.1 cm to 2 cm, or from 0.5 cm to 2 cm, for example from 1 cm to 1.5 cm.

The magnetic field source may be a permanent magnet, such as a rare-earth magnet. Rare-earth magnets include, but are not limited to, samarium-cobalt magnets (e.g., $SmCo_5$), neodymium alloy (NdFeB) magnets (e.g., $Nd_2Fe_{14}B$), and the like.

In certain embodiments, the magnetic field source produces a magnetic field ranging from 0.01 T to 10 T, or from 0.01 T to 5 T, or from 0.01 T to 2 T, or from 0.1 T to 2 T, or from 0.1 T to 1.5 T, including from 0.1 T to 1 T. In some cases, the magnetic field source is configured to produce a magnetic field with a magnetic field gradient (e.g., an absolute field gradient) ranging from 0.1 T/mm to 10 T/mm, such as from 0.1 T/mm to 7 T/mm, or from 0.1 T/mm to 5 T/mm, or from 0.1 T/mm to 3 T/mm, such as from 0.1 T/mm to 2 T/mm, including from 0.1 T/mm to 1 T/mm. In certain instances, the magnetic field source produces a magnetic field having a magnetic field gradient such that the product of the magnetic field and the magnetic field gradient (e.g., absolute field gradient) ranges from 0.001 $T^2$/mm to 100 $T^2$/mm, such as from 0.01 $T^2$/mm to 75 $T^2$/mm, including from 0.1 $T^2$/mm to 50 $T^2$/mm, or from 0.1 $T^2$/mm to 25 $T^2$/mm, or from 0.1 $T^2$/mm to 10 $T^2$/mm, or from 0.1 $T^2$/mm to 5 $T^2$/mm, or from 0.1 $T^2$/mm to 3 $T^2$/mm, such as from 0.1 $T^2$/mm to 2 $T^2$/mm, including from 0.1 $T^2$/mm to 1 $T^2$/mm.

Magnetic Field Guides

Aspects of the device for separating magnetically labeled moieties in a sample also include one or more magnetic field guides. The magnetic field guide may be configured to direct the magnetic field from the magnetic field source to the sample flow path. In certain instances, the magnetic field guide is configured to focus the magnetic field produced by the magnetic field source. The magnetic field guide may focus the magnetic field by increasing the magnetic flux of the magnetic field source, where the magnetic flux is the amount of magnetic field (e.g., the magnetic field density) that passes through a given surface area. The magnetic flux may depend on the magnetic field strength, the area of the surface and the angle between the magnetic field and the surface. For example, the magnetic field guide may focus the magnetic field, and thus increase the magnetic flux, by directing the magnetic field through a smaller area. In some cases, directing the magnetic field through a smaller area increases the magnetic field density, thus resulting in an increase in the magnetic flux. The magnetic field source and the magnetic field guide may be configured to produce a magnetic flux sufficient to separate magnetically labeled moieties from non-magnetically labeled moieties in a sample. In some instances, the magnetic field guide is configured to produce a magnetic field having a magnetic flux density ranging from 0.01 T to 10 T, or from 0.01 T to 5 T, or from 0.01 T to 2 T, such as from 0.1 T to 2 T, including from 0.5 T to 1.5 T.

In certain cases, the magnetic field guide is configured to direct the magnetic field from the magnetic field source to the sample flow path with minimal loss in magnetic flux. In some cases, the magnetic field guide is configured to direct the magnetic field from the magnetic field source to the sample flow path with substantially no loss in magnetic flux. Without any intent to be bound by theory, the magnetic field guide may be configured to minimize the decrease in magnetic flux due to the self-demagnetization fields present in a soft magnet near the surfaces of the soft magnet. For example, the magnetic field guide may be configured to direct the magnetic field from the magnetic field source to the sample flow path with a decrease in magnetic flux of 50% or less from the initial magnetic flux, such as 40% or less, including 30% or less, or 25% or less, or 20% or less, or 15% or less, or 10% or less, or 7% or less, or 5% or less, for example 3% or less, or 2% or less, or 1% or less from the initial magnetic flux.

In certain embodiments, the magnetic field guide is configured to focus the magnetic field by having portion with a tapered shape and by directing the magnetic field from the magnetic field source through the tapered portion of the magnetic field guide. By "tapered" is meant that a portion of the magnetic field guide has a wider end with a larger cross-sectional area and the cross-sectional area of the portion of the magnetic field guide becomes progressively smaller towards a narrower opposing end of the magnetic field guide. For example, the magnetic field guide may have a wedge-shaped portion, where the base of the wedge-shaped portion has an area. Cross-sections of the wedge-shaped portion taken parallel to the base of the wedge-shaped portion will have progressively smaller areas towards the end of the wedge-shaped portion opposite from the base (i.e., towards the apex edge of the wedge-shaped portion).

In some instances, the magnetic field guide has a wedge-shaped portion and is configured to direct the magnetic field from the base of the wedge-shaped portion to the apex edge of the wedge-shaped portion. Directing the magnetic field from the base of the wedge-shaped portion to the apex edge of the wedge-shaped portion may facilitate an increase in the magnetic flux of the magnetic field from the magnetic field source, as described above. An increase in the magnetic flux at the apex edge of the wedge-shaped portion of the magnetic field guide may produce a higher magnetic field and a higher magnetic field gradient proximal to the apex edge of the magnetic field guide than would be present in the absence of the magnetic field guide. Other tapered shapes for the magnetic field guide are possible, such as, but not limited to, pyramid, cone, frustum, combinations thereof, and the like.

In some instances, the magnetic field guide includes a portion that tapers to a point or an edge (e.g., the apex edge). For example, a cross-sectional profile of the magnetic field guide may taper to a point at the apex edge of the magnetic field guide. In other embodiments, the cross-sectional profile of the magnetic field guide tapers to a rounded edge such that the apex edge has a rounded (e.g., arcuate) cross-sectional profile at the apex edge. The term "wedge-shaped" as used herein is meant to include embodiments of the magnetic field guide that have an apex edge with a cross-sectional profile that tapers to a point at the apex edge. The term "wedge-shaped" also includes embodiments of the magnetic field guide that have an apex edge with a cross-sectional profile that does not taper to a point at the apex edge. For example, the apex edge of the magnetic field guide may have a cross-sectional profile that is rounded, truncated, blunted, and the like. The apex edge of the magnetic field guide may have a width that is approximately the same as the width (or diameter) of a conduit positioned adjacent the apex edge of the magnetic field guide. In certain embodiments, the apex edge of the magnetic field guide has a width that is less than the width (or diameter) of the conduit. In some cases, the width of the apex edge of the magnetic field guide is 5 mm or less, such as 4 mm or less, or 3 mm or less, or 2 mm or less, or 1 mm or less, or 0.5 mm or less, or 0.1 mm or less.

In certain instances, the apex edge of a wedge-shaped portion of the magnetic field guide has an apex angle, where the apex angle is the angle between the two faces of magnetic field guide that meet at the apex edge. In some cases, the apex angle is 150 degrees or less, or 135 degrees or less, such as 120 degrees or less, or 105 degrees or less, including 90 degrees or less, or 75 degrees or less, or 60 degrees or less, or 45 degrees or less, for example 30 degrees or less. In some embodiments, the apex angle is 60 degrees.

In certain embodiments, the apex edge of the magnetic field guide may be substantially parallel to a longitudinal axis of the magnetic field guide. In addition, the apex edge of the magnetic field guide may be substantially parallel to a longitudinal axis of the magnetic field source. In embodiments with one magnetic field source, the magnetic field source may have one or more magnetic field guides associated with the magnetic field source. For example, the magnetic field source may have a first magnetic field guide and a second magnetic field guide associated with the magnetic field source. In some embodiments, the device includes a first magnetic field guide disposed on a first surface of the magnetic field source, and a second magnetic field guide disposed on a second surface of the same magnetic field source. In some instances, the first and second magnetic field guides are disposed on opposite surfaces of the magnetic field source. In certain embodiments, the first magnetic field guide is wedge-shaped with a first apex edge, the second magnetic field guide is wedge-shaped with a second apex edge, and the first apex edge is aligned substantially across from and parallel to the second apex edge. The first apex edge may be positioned at a substantially uniform distance along its length from the second apex edge. In some cases, the magnetic field source includes a permanent magnet, as described above, and the first and second surfaces of the magnetic field source are the north and south poles of the magnetic field source.

In embodiments with more than one magnetic field source, each magnetic field source may have a magnetic field guide associated with it. Each magnetic field guide may be positioned such that the longitudinal axis of the magnetic field guide is substantially parallel to the longitudinal axis of the magnetic field source to which it is associated.

In certain embodiments, the apex edge of the magnetic field guide has a linear profile. By "linear" is meant that the apex edge of the magnetic field guide is substantially straight. In some instances, the apex edge of the magnetic field guide has a non-linear profile, such as, but not limited to, a saw-tooth, sinusoidal, square wave, triangular wave profile, combinations thereof, and the like. A magnetic field guide that has an apex edge with a non-linear profile may facilitate a local increase in the magnetic field and/or the magnetic field gradient near the non-linear portions of the apex edge.

The magnetic field guide may be proximal to the magnetic field source. In certain cases, the magnetic field guide is contacted with the magnetic field source. For example, the magnetic field guide may be attached to the magnetic field source to facilitate contact between the magnetic field guide and the magnetic field source. As described above, the device may include one magnetic field source. In these embodiments, the magnetic field source may include a wedge-shaped portion as described above. The magnetic field source may also include an extended portion between the wedge-shaped portion and the magnetic field source. The extended portion of the magnetic field guide may be configured to position the wedge-shaped portion at a distance away from the surface of the magnetic field source. For example, the extended portion of the magnetic field guide may contact the magnetic field source on a part of a first surface of the extended portion of the magnetic field guide. The extended portion of the magnetic field guide may extend a distance above the top surface of the magnetic field source. The part of the first surface of the extended portion of the magnetic field guide that extends above the top surface of the magnetic field source may have the wedge-shaped portion of the magnetic field guide. In some embodiments, the extended portion and the wedge-shaped portion of the magnetic field guide are contiguous (e.g., formed from the same piece of material). In other cases, the extended portion and the wedge-shaped portion of the magnetic field guide are separate pieces that are attached to each other. As described above, the device may also include a second magnetic field guide disposed on a surface of the magnetic field source opposite from the first magnetic field guide. Similar to the first magnetic field guide described above, the second magnetic field guide may include an extended portion and a wedge-shaped portion. The first and second magnetic field guides may be configured such that the apex edge of the wedge-shaped portion of the first magnetic field guide is proximal to the apex edge of the wedge-shaped portion of the second magnetic field guide. In some cases, the apex edge of the first magnetic field guide is substantially parallel to the apex edge of the second magnetic field guide. The apex edge of the first magnetic field guide may be aligned across from the apex edge of the second magnetic field guide. For example, the apex edge of the first magnetic field guide may be aligned substantially directly across from the apex edge of the second magnetic field guide. In certain embodiments, the apex edge of the first magnetic field guide is aligned substantially across from and substantially parallel to the apex edge of the second magnetic field guide. During use, the distance between the apex edge of the first magnetic field guide and the apex edge of the second magnetic field guide may be 5 cm or less, such as 2 cm or less, including 1 cm or less, or 7 mm or less, or 5 mm or less, or 3 mm or less, or 2 mm or less, or 1 mm or less.

In other embodiments as described above, the device may include two magnetic field sources, such as first and second magnetic field sources arranged proximal to each other. In some instances, a first magnetic field guide is associated with the first magnetic field source, and a second magnetic field guide is associated with the second magnetic field source. The first magnetic field guide may be positioned on the first magnetic field source on the surface of the first magnetic field source proximal to the second magnetic field source. For example, in embodiments where the magnetic field guides are wedge-shaped, the first magnetic field guide may be disposed on the first magnetic field source such that the base of the first magnetic field guide contacts the surface of the first magnetic source proximal to the second magnetic source. Similarly, the second magnetic field guide may be positioned on the second magnetic field source on the surface of the second magnetic field source proximal to the first magnetic field source. For example, in embodiments where the magnetic field guides are wedge-shaped, the second magnetic field guide may be disposed on the second magnetic field source such that the base of the second magnetic field guide contacts the surface of the second magnetic source proximal to the first magnetic source. In this arrangement, the first and second magnetic field guides may be positioned between the first and second magnetic field sources. In addition, the apex edge of the first magnetic field guide may be proximal to the apex edge of the second magnetic field guide. In some cases, the apex edge of the first magnetic field guide is substantially parallel to the apex edge of the second magnetic field guide. The apex edge of the first magnetic field guide may be aligned across from the apex edge of the second magnetic field guide. For example, the apex edge of the first magnetic field guide may be aligned substantially directly across from the apex edge of the second magnetic field guide. In certain embodiments, the apex edge of the first magnetic field guide is aligned substantially across from and substantially parallel to the apex edge of the second magnetic field guide. During use, the distance between the apex edge of the first magnetic field guide and the apex edge of the second magnetic field guide may be 5 cm or less, such as 2 cm or less, including 1 cm or less, or 7 mm or less, or 5 mm or less, or 3 mm or less, or 2 mm or less, or 1 mm or less.

As described above, the first and second magnetic field guides may be configured to focus the magnetic field produced by the magnetic field source. In certain instances, the first and second magnetic field guides focus the magnetic field to a region proximal to the apex edges of the first and second magnetic field guides. For example, the first and second magnetic field guides may focus the magnetic field in an area between the apex edges of the magnetic field guides. The first and second magnetic field guides may be configured to produce a magnetic flux proximal to the apex edges of the magnetic field guides sufficient to separate magnetically labeled moieties from non-magnetically labeled moieties in a sample. In some instances, the first and second magnetic field guides are configured to produce a magnetic field proximal to the apex edges of the magnetic field guides having a magnetic flux density ranging from 0.01 T to 10 T, or from 0.01 T to 5 T, or from 0.01 T to 2 T, such as from 0.1 T to 2 T, including from 0.5 T to 1.5 T.

In certain embodiments, the magnetic field guide includes a soft magnet. The term "soft magnet" refers to a material that can be magnetized in the presence of an applied external magnetic field, but whose magnetism substantially decreases when the external magnetic field is removed. Soft magnets may include, but are not limited to, ferromagnetic materials, such as iron (e.g., annealed iron), stainless steel and nickel, ferrimagnetic materials, such as ceramic oxides of metals, combinations thereof, and the like.

In some instances, the magnetic field guide may have a length ranging from 1 cm to 100 cm, such as from 1 cm to 75 cm, including from 1 cm to 50 cm, or from 1 cm to 25 cm, or from 1 cm to 10 cm, or from 5 cm to 10 cm, for example from 5 cm to 6 cm; a width ranging from 0.1 cm to 100 cm, such as from 0.1 cm to 75 cm, including from 0.1 cm to 50 cm, or from 0.1 cm to 25 cm, or form 0.1 cm to 10 cm, or from 0.1 cm to 5 cm, or from 0.1 cm to 2 cm, or from 0.5 cm to 2 cm, for example from 1 cm to 1.5 cm; and a height ranging from 0.1 cm to 100 cm, such as from 0.1 cm to 75 cm, including from 0.1 cm to 50 cm, or from 0.1 cm to 25 cm, or from 0.1 cm to 10 cm, or from 0.1 cm to 5 cm, or from 0.1 cm to 2 cm, or from 0.5 cm to 2 cm, for example from 1 cm to 1.5 cm.

Figure 1B:
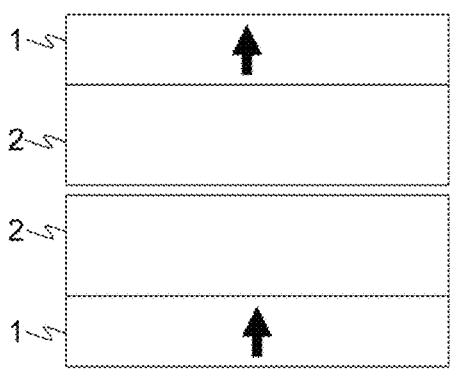
FIG. 1(b) shows a schematic of a side view of a magnetic separation device that includes two magnetic field sources, according to embodiments of the present disclosure.
Figure 1C:
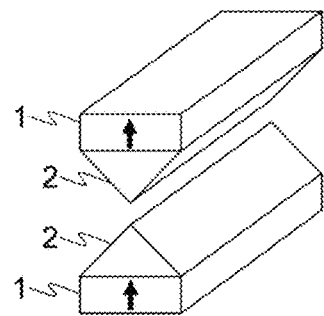
FIG. 1(c) shows a schematic of a three-dimensional perspective view of a magnetic separation device that includes two magnetic field sources, according to embodiments of the present disclosure.

An example of an embodiment of a magnetic separation device according to the present disclosure is shown in the schematic illustrations in FIGS. 1(a), 1(b) and 1(c). The device includes two soft magnetic field guides 2. Each magnetic field guide 2 is attached to a permanent magnet 1. The two soft magnetic field guides 2 have a tapered shape from the end attached to the permanent magnet 1 towards the apex edges of the two magnetic field guides that are directly opposite each other. The apex edges of the magnetic field guides 2 are substantially linear, as shown in FIGS. 1(b) and 1(c). The permanent magnets 1 have magnetizations 12 that are in the same direction and perpendicular to the interface between the permanent magnets 1 and the magnetic field guides 2. The magnetic field guides 2 and permanent magnets 1 form a permanent magnet driven magnetic flux concentration structure, where the magnetic flux from permanent magnets 1 is focused (e.g., increased) by the tapered shape of the magnetic field guides 2. The magnetic field guides 2 produce a locally high magnetic flux density in the area proximal to the apex edges of the magnetic field guides. In certain instances, the high magnetic flux produces a high magnetic field and magnetic field gradient in the area proximal to, such as near and/or between, the apex edges of the magnetic field guides.

Figure 4A:
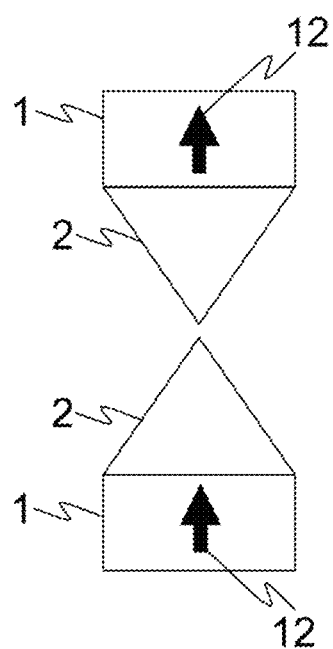
FIG. 4(a) shows a schematic of a front view of a magnetic separation device, according to embodiments of the present disclosure.
Figure 4B:
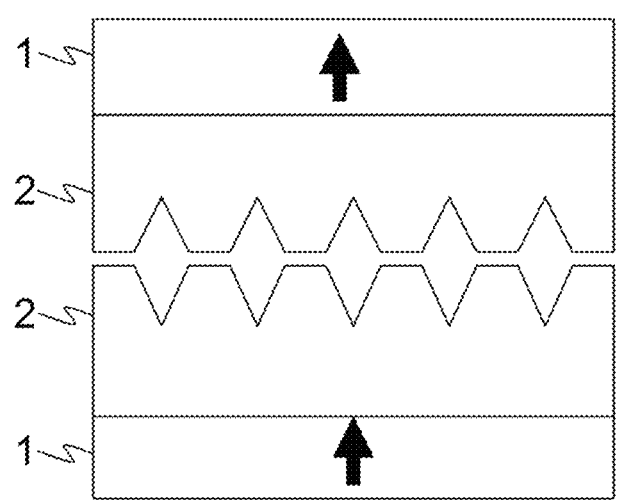
FIG. 4(b) shows a schematic of a side view of a magnetic separation device having magnetic field guides with a saw-tooth shaped profile, according to embodiments of the present disclosure.

Another embodiment of the magnetic separation device is shown in FIGS. 4(a) and 4(b). As shown in FIG. 4(a), the arrangement of the magnetic field sources (e.g., permanent magnets) 1 and the magnetic field guides 2 is the same as in FIG. 1(a). However, as shown in FIG. 4(b), rather than having a linear profile, the magnetic field guides 2 have apex edges with a saw-tooth profile. In certain embodiments, the corners along the saw-tooth apex edge have a locally enhanced magnetic field and magnetic field gradient, which may facilitate the separation of magnetic labels and magnetically labeled moieties from non-magnetically labeled moieties in the sample.

Figure 8A:
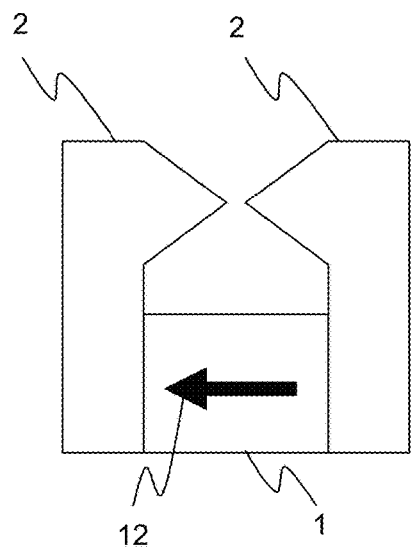
FIG. 8(a) shows a schematic of a front view of a magnetic separation device that includes one magnetic field source, according to embodiments of the present disclosure.
Figure 8B:
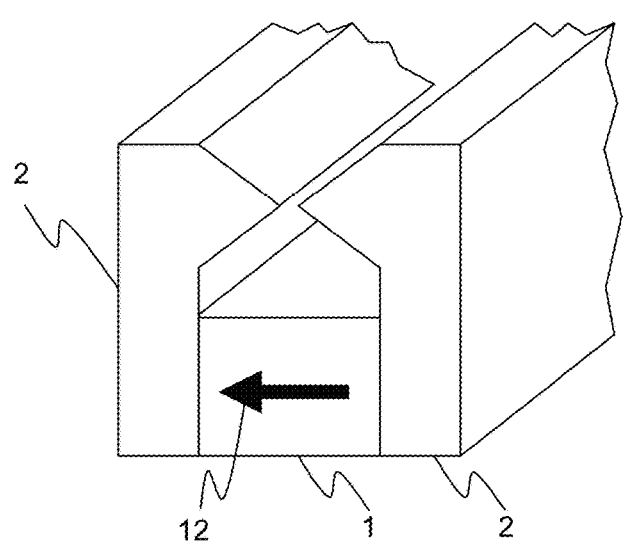
FIG. 8(b) shows a schematic of a three-dimensional perspective partial view of a magnetic separation device that includes one magnetic field source, according to embodiments of the present disclosure.

Another embodiment of a magnetic separation device is shown in the schematic illustrations in FIGS. 8(*a*) and 8(*b*). The device includes two soft magnetic field guides 2. The magnetic field guides 2 are attached to opposing sides of the same permanent magnet 1. The magnetic field guides 2 each have a wedge-shaped portion with a tapered shape. The wedge-shaped portions of the magnetic field guides 2 have cross-sectional areas that decrease towards the apex edges of the magnetic field guides. The apex edges of the magnetic field guides 2 are substantially linear and positioned directly opposite each other. The permanent magnet 1 has a magnetization 12 that is perpendicular to the interfaces between the permanent magnet 1 and the magnetic field guides 2. The magnetic field guides 2 and permanent magnet 1 form a permanent magnet driven magnetic flux concentration structure, where the magnetic flux from permanent magnet 1 is focused (e.g., increased) by the tapered shape of the wedge-shaped portions of the magnetic field guides 2. The magnetic field guides 2 produce a locally high magnetic flux density in the area proximal to (e.g., near and/or between) the apex edges of the magnetic field guides. In certain instances, the high magnetic flux produces a high magnetic field and magnetic field gradient in the area proximal to the apex edges of the magnetic field guides.

In certain embodiments, the device includes one or more magnetic flux sinks. The magnetic flux sink may be disposed on a surface of the magnetic field source. In some instances, the magnetic flux sink is disposed on a surface of the magnetic field source opposite the surface of the magnetic field source in contact with the magnetic field guide. In certain cases, the magnetic flux sink is configured to increase the magnetic field of the magnetic field source. The magnetic flux sink may be configured to increase the magnetic field of the magnetic field source by decreasing the self-demagnetization field of the magnetic field source (e.g., the self-demagnetization field of the permanent magnet). In some cases, the magnetic flux sink includes a soft magnet.

Conduit

Embodiments of the device for separating magnetically labeled moieties in a sample may further include a conduit. The conduit may be configured to direct a flow of the sample through the device. As such, the conduit may be configured to carry the flow of the sample (e.g., a sample solution) in a channel, tube, well, etc. In certain embodiments, the conduit is enclosed, such that the conduit is defined by outer walls that surround a central flow path. The central flow path may be aligned with a longitudinal axis of the conduit. The central flow path may have any convenient shape, such as, but not limited to, a flow path with a cross-sectional profile of a circle, an ellipse, a square, a rectangle, a pentagon, a hexagon, an irregular cross-sectional profile, combinations thereof, and the like. During use, the conduit may also be configured to retain the magnetically labeled moieties in the sample.

In some instances, at least a portion of the conduit is positioned between the magnetic field guides, such as between the first magnetic field guide and the second magnetic field guide. The conduit may be positioned between the first and second magnetic field guides such that a longitudinal axis of the conduit is substantially parallel to a longitudinal axis of the first magnetic field guide and a longitudinal axis of the second magnetic field guide. For example, the conduit may be positioned between the apex edges of the first and second magnetic field guides such that the longitudinal axis of the conduit is substantially parallel to the apex edges of each of the first and second magnetic field guides. In some cases, positioning the conduit substantially parallel to the apex edges of the magnetic field guides maximizes the length of conduit, and thus the flow of sample fluid, that is between the apex edges of the magnetic field guides. In certain instances, positioning the conduit substantially parallel to the apex edges of the magnetic field guides maximizes the amount of time the flow of the sample is between the magnetic field guides. Aligning the conduit substantially parallel to the apex edges of the magnetic field guides may facilitate retaining the magnetically labeled moieties in the conduit.

In some instances, at least a portion of the conduit is positioned proximal to the magnetic field guides, such as adjacent the first magnetic field guide and the second magnetic field guide. In some instances, the conduit is positioned adjacent to, but not between, the apex edges of the first and second magnetic field guides. In certain cases, the conduit is positioned such that the conduit is in direct contact with an outer surface of one or more of the magnetic field guides. For example, the conduit may be positioned such that the conduit contacts the angled outer surface of the wedged-shaped portion of the magnetic field guides. In some cases, the conduit may not be positioned directly between the apex edges of the magnetic field guides, but rather adjacent to the apex edges and contacting an outer surface of the magnetic field guides as described above. The conduit may be positioned proximal to the first and second magnetic field guides such that a longitudinal axis of the conduit is substantially parallel to a longitudinal axis of the first magnetic field guide and a longitudinal axis of the second magnetic field guide. For example, the conduit may be positioned adjacent to the first and second magnetic field guides such that the longitudinal axis of the conduit is substantially parallel to the apex edges of each of the first and second magnetic field guides. In some cases, positioning the conduit substantially parallel to the apex edges of the magnetic field guides maximizes the length of conduit, and thus the flow of sample fluid, that is adjacent to the apex edges of the magnetic field guides. In certain instances, positioning the conduit substantially parallel to the apex edges of the magnetic field guides maximizes the amount of time the flow of the sample is proximal to the magnetic field guides. Aligning the conduit substantially parallel to the apex edges of the magnetic field guides may facilitate retaining the magnetically labeled moieties in the conduit.

In some instances, the conduit is configured to have a narrower cross-sectional area in the portion of the conduit positioned between the magnetic field guides. For example, the cross-sectional area of the conduit upstream from the portion of the conduit positioned between the magnetic field guides may be greater than the cross-sectional area of the portion of the conduit positioned between the magnetic field guides. Similarly, the cross-sectional area of the conduit downstream from the portion of the conduit positioned between the magnetic field guides may be greater than the cross-sectional area of the portion of the conduit positioned between the magnetic field guides. Thus, in some cases, a portion of the conduit positioned between the first and second magnetic field guides has a cross-sectional area less than the cross-sectional area of a portion of the conduit upstream or downstream from the portion of the conduit positioned between the first and second magnetic field guides.

In certain embodiments, the conduit may be positioned between the magnetic field guides manually. For example, the conduit may be manually aligned between the magnetic field guides, and may be manually removed from between the magnetic field guides. The conduit may be configured to have one or more alignment guides on the exterior of the conduit, such as, but not limited to, a notch, a tab, a groove, a guide post, etc., which may facilitate positioning of the conduit between the magnetic field guides. In some embodiments, the device may be configured to automatically position the conduit between the magnetic field guides. The conduit may include one or more markings or alignment guides as described above that the device may use to position the conduit between the magnetic field guides.

In some instances, the conduit is configured to be positionable away from the magnetic field, e.g., positionable away from the magnetic field sources and the magnetic field guides. Positioning the conduit away from the magnetic field may facilitate the recovery of magnetically labeled moieties that were retained in the conduit during an assay. In certain cases, the device may be configured to automatically position the conduit away from the magnetic field guides.

In certain cases, the conduit is configured to be reusable. A reusable conduit may be configured to be washed between assays, such as, but not limited to, configured to be washed by flowing a wash solution or buffer through the conduit between assays. In some cases, the conduit may be configured to be washed and reused without removing the conduit from the device. In other cases, the conduit may be configured to be removed from the device, washed and then reinserted into the device for a subsequent assay. In certain embodiments, the conduit is configured to be disposable. By disposable is meant that the conduit may be used once or several times (e.g., 20 times or less, 15 times or less, 10 times or less, or 5 times or less) and then discarded and replaced by a new conduit. For example, the conduit may be configured to be a single-use conduit, where the conduit is configured to be used for a single assay, and then removed and discarded. A new conduit may be used in a subsequent assay.

In certain embodiments, the conduit may have a height (e.g., for conduits that do not have a round cross-sectional profile) or an inner diameter (e.g., for conduits that have a round cross-sectional profile) of 5 cm or less, such as 2 cm or less, including 1 cm or less, or 7 mm or less, or 5 mm or less, or 3 mm or less, or 2 mm or less, or 1 mm or less. The length of the conduit may range from 1 cm to 1000 cm, such as from 2 cm to 750 cm, including from 5 cm to 500 cm, or from 5 cm to 250 cm, or from 10 cm to 100 cm, such as from 10 cm to 50 cm, for example from 10 cm to 25 cm.

In certain embodiments, the conduit is configured to be substantially free from magnetic gradient enhancing materials. For example, the conduit may be made of non-magnetic and/or non-magnetizable materials. In some instances, the central flow path of the conduit is substantially free from magnetic gradient enhancing materials (excluding the magnetic labels themselves). For instance, the central flow path of the conduit may be substantially free of any materials (e.g., matrix materials, magnetizable particles (e.g., magnetizable spheres/ellipsoids), magnetizable wires, magnetizable cylinders, and the like) other than the sample (e.g., including any buffer and magnetic labels, etc. used in the assay itself). In some instances, having a conduit with a central flow path substantially free of materials, such as magnetizable materials, facilitates the subsequent recovery of the separated magnetically labeled moieties. For example, the separated magnetically labeled moieties may be more easily flushed from the conduit when the conduit is substantially free of materials as compared to a conduit with materials, such as magnetizable materials, in the central flow path of the conduit. The separated magnetically labeled moieties may be more easily flushed from the conduit, for instance, due to the absence of restrictions to the fluid flow path in a conduit substantially free of materials and/or the absence of magnetizable materials in the flow path that may have remnant magnetizations that retain the magnetically labeled moieties in the conduit.

In certain embodiments, the conduit includes a material that is flexible. When positioned between the magnetic field guides, the magnetic field guides, in some instances, may contact the surface of the conduit. In some cases, the first magnetic field guide (e.g., the apex edge of the first magnetic field guide) contacts a surface of the conduit, and the second magnetic field guide (e.g., the apex edge of the second magnetic field guide) contacts an opposing surface of the conduit. The magnetic field guides may be configured to contact the surfaces of the conduit without exerting significant pressure on the conduit. In other embodiments, the device is configured to compress the conduit between the apex edge of the first magnetic field guide and the apex edge of the second magnetic field guide. In some instances, the conduit is compressed such that the height (e.g., inner diameter) of the conduit is compressed to a fraction of the height of the conduit in the absence of any compression. For example, the conduit may be compressed to 90% or less of its initial height, such as 80% or less, including 70% or less, or 60% or less, or 50% or less of its initial height. In certain embodiments, the conduit is configured such that the conduit may be compressed near the center of the conduit, but may retain substantially the same height towards the outer edges of the conduit. In these embodiments, under compression, the conduit may have a central flow path with a height less than the height of the flow path near the outer edges of the conduit. Having a central flow path with a height less than the height of the flow path near the outer edges of the conduit may facilitate the retention of the magnetically labeled moieties in the conduit because the flow rate through the narrower center flow path of the conduit may be less than the flow rate through the wider periphery of the conduit.

The conduit may be made of any material that is compatible with the assay conditions, e.g., the sample solution buffer, pressure, temperature, etc. For example, the conduit may include materials that are substantially non-reactive to the sample, the moieties in the sample, the buffer, and the like. The conduit may include a flexible material, such that the conduit is flexible. In certain instances, the conduit is configured to deform from its initial shape and/or stretch if the conduit is compressed between the apex edges of the magnetic field guides, as described above. The conduit may be configured to deform from its initial shape and/or stretch without breaking, splitting, tearing, etc., when the conduit is compressed between the magnetic field guides. In some instances, the conduit includes glass, or polymers, such as, but not limited to, silicone, polypropylene, polyethylene, polyether ether ketone (PEEK), and the like. In certain embodiments, the conduit includes a flexible material, such as a flexible polymer material (e.g., silicone, polyethylene, polypropylene, PEEK, etc.).

In some instances, the conduit has a cover layer disposed on the outer surface of the conduit. The cover layer may be configured to protect the conduit from the surrounding environment, and in some instances, may include one or more alignment guides to facilitate positioning the conduit between the magnetic field guides, as described above. The cover layer may include a flexible material, such that the cover layer is flexible and may deform from its initial shape and/or stretch. In certain instances, the cover layer is configured to deform from its initial shape and/or stretch if the conduit is compressed between the apex edges of the magnetic field guides as described above. The cover layer may be configured to deform from its initial shape and/or stretch without breaking, splitting, tearing, etc., when the conduit is compressed between the magnetic field guides. In certain embodiments, the conduit includes a flexible material, such as a flexible polymer material (e.g., silicone, polyethylene, polypropylene, PEEK, etc.).

An example of a conduit according to embodiments of the present disclosure is shown in FIGS. 2(a) and 2(b). The conduit 20 has a central flow path 22 configured to carry a flow of a sample through the device. The conduit may be configured with a rectangular cross-sectional profile (see FIG. 2(b)). In some instances, a conduit with a rectangular cross-sectional profile may facilitate alignment of the conduit between the magnetic field guides of the device.

Figure 3A:
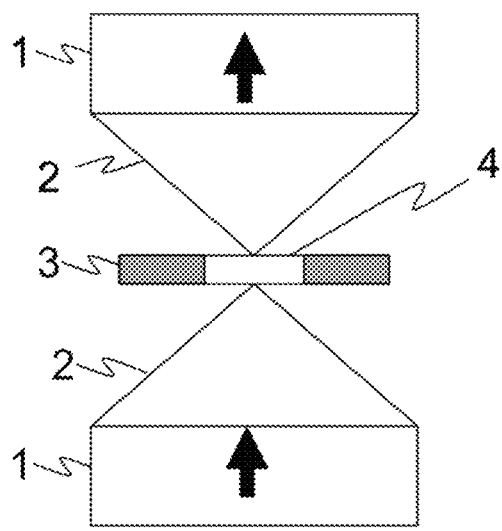
FIGS. 3(a) and 3(b) show schematics of front views of a conduit positioned between the magnetic field guides in a magnetic separation device, according to embodiments of the present disclosure.
Figure 3B:
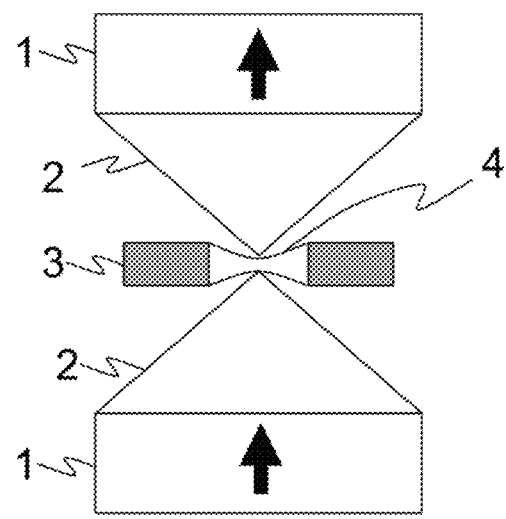

FIGS. 3(a) and 3(b) show schematics of front views of a conduit positioned between the magnetic field guides in a magnetic separation device, according to embodiments of the present disclosure. The conduit 3 is positioned within the gap between the opposing apex edges of the magnetic field guides as shown in FIGS. 3(a) and 3(b). A liquid sample with magnetically labeled biological or chemical moieties flows within the conduit 3 and along the tapered apex edges of the magnetic field guides. The magnetic field and magnetic field gradient produced by the magnetic field sources attracts the magnetic labels and magnetically labeled moieties from the flowing sample. The magnetic labels and magnetically labeled moieties are then pulled to and are retained at the inner surface of the conduit proximal to the apex edges of the magnetic field guides. Thus, magnetic labels and magnetically labeled moieties are separated from the flowing solution and retained within the conduit. After the solution sample is flowed through the conduit and a plurality of magnetic labels and magnetically labeled moieties are separated from the flowing solution, conduit 3 is then removed from the gap between the magnetic field guides 2 and the magnetic field within the conduit becomes approximately zero. By flushing the retained magnetic labels and magnetically labeled moieties within the conduit from the conduit with a buffer solution, the magnetic labels and magnetically labeled moieties can then be recovered from the conduit.

FIG. 3(a) shows an embodiment where the conduit 3 has a rectangular center flow path, where the magnetic labels and magnetically labeled moieties are retained towards center of the conduit. FIG. 3(b) shows an embodiment where the conduit has a pinched center flow path (e.g., the center flow path has a height less than the height of the flow path near the periphery of the flow path). In FIG. 3(b), magnetic labels and magnetically labeled moieties are retained near the pinched center portion of the flow path. In certain instances, because the side areas of the conduit have a larger clearance height than the pinched center flow path, when solution flows within the conduit, the solution flowing through the center part of the conduit experiences a slower flow rate than solution flowing through the side areas. Thus, in some cases, the magnetic labels and magnetically labeled moieties experience less flow sheer force than in the embodiment shown in FIG. 3(a), which may facilitate magnetic speration efficiency.

FIGS. 6(a), 6(b) and 6(c) show graphs of a simulated magnetic field (FIG. 6(a)), magnetic field gradient (FIG. 6(b)), and product of the magnetic field and absolute magnetic field gradient (FIG. 6(c)) across the gap between the magnetic field guides as shown in FIG. 1(a) for a magnetic separation device with a distance between the apex edges of the magnetic field guides of 1.4 mm, according to embodiments of the present disclosure. The x-axis is along the center of the gap from left to right between the apex edges of the magnetic field guides, as shown in FIG. 3(a). FIG. 6(a) shows that a magnetic field of 1.4 Tesla or more can be achieved in certain embodiments. FIG. 6(b) shows a graph of the magnetic field gradient calculated from the magnetic field profile shown in FIG. 6(a), where the gradient peak is 0.8 T/mm or more across the gap between the apex edges of the magnetic field guides. The gradient values indicate a strong magnetic force on the magnetic labels towards the apex edges of the magnetic field guides. FIG. 6(c) shows a graph of the product of the magnetic field and absolute magnetic field gradient, which is proportional to the magnetic force on the magnetically labeled moieties flowing through the conduit. In some instances, the magnetically labeled moieties within the conduit are attracted and retained within +/−0.5 mm of the apex edge of the magnetic field guide.

Figure 5:
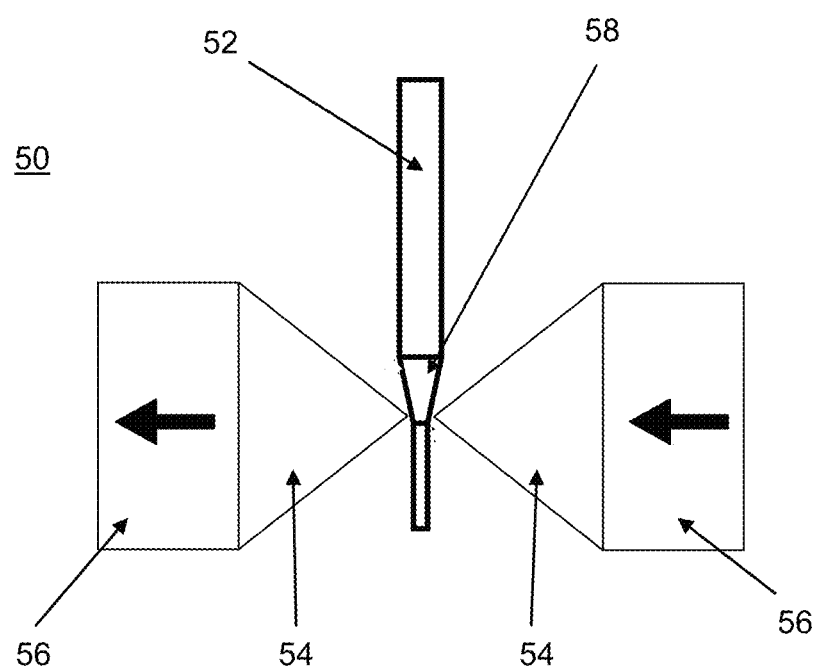
FIG. 5 shows a schematic of a conduit positioned transverse to the magnetic field guides, according to embodiments of the present disclosure.
Figure 7:
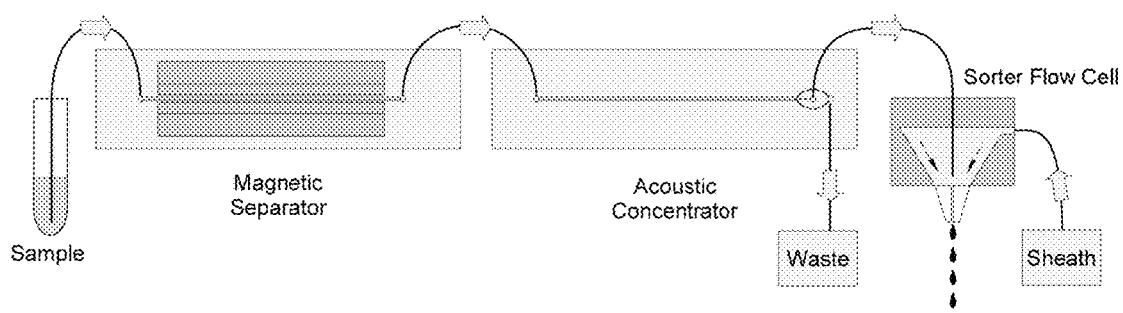
FIG. 7 shows a schematic of a system including a magnetic separation device, an acoustic concentrator and a flow cytometer, according to embodiments of the present disclosure.

FIG. 5 illustrates another embodiment of a conduit positioned in a magnetic separation device according to embodiments of the present disclosure. FIG. 5 shows a schematic of a magnetic separation device 50 with a conduit 52 having a flow path 58 positioned between the magnetic field guides 54 and the magnetic field sources (e.g., permanent magnets) 56. The conduit flow path 58 shown in FIG. 5 has a tapered cross-sectional shape such that the cross-sectional dimension of the conduit proximal to the apex edges of the magnetic field guides is less than the cross-sectional dimension distal to the apex. This allows the apexes of to be positioned closer together, and, further, facilitates positioning of the conduit 52 between the apex edges of the magnetic field guides 54.

Conduit Holder

In certain embodiments, the device includes a conduit holder operatively coupled to the conduit. In some cases, the conduit holder is configured to operatively couple the conduit to the magnetic separation device. For example, the conduit holder may be configured to facilitate positioning of the conduit between the magnetic field guides. In some cases, the conduit holder includes an elongated tab attached to the exterior of the conduit. The elongated tab may be attached to the exterior of the conduit such that the elongated tab is substantially parallel to a longitudinal axis of the conduit. In certain instances, the conduit holder facilitates positioning the conduit in the magnetic separation device such that a longitudinal axis of the conduit is substantially parallel to a longitudinal axis of the magnetic separation device, such as substantially parallel to the apex edges of the magnetic field guides as described above.

In some cases, the magnetic separation is configured to mate with the conduit holder operatively coupled to the conduit. For example, the magnetic separation device may be configured to have one or more mating elements, such as, but not limited to, a notch, a tab, a groove, a channel, a guide post, etc., which correspond to one or more corresponding alignment guides on the conduit holder. The one or more mating elements may facilitate positioning the conduit between the magnetic field guides of the magnetic separation device. In some cases, the magnetic separation device includes a channel configured to mate with the conduit holder. The channel may be configured to position the conduit holder in the magnetic separation device such that the longitudinal axis of the conduit is substantially parallel to a longitudinal axis of the magnetic separation device, such as substantially parallel to the apex edges of the magnetic field guides as described above.

In certain embodiments, the conduit holder may be positioned between the magnetic field guides manually. For example, the conduit holder may be manually positioned in the magnetic separation device by aligning the conduit holder with the corresponding mating element (e.g., channel) of the magnetic separation device. In some cases, the conduit holder may be manually removed from the magnetic separation device. In some embodiments, the device may be configured to automatically position the conduit holder in the magnetic separation device. The conduit holder may include one or more markings or alignment guides as described above that the device may use to automatically position the conduit holder in the magnetic separation device.

Figure 9:
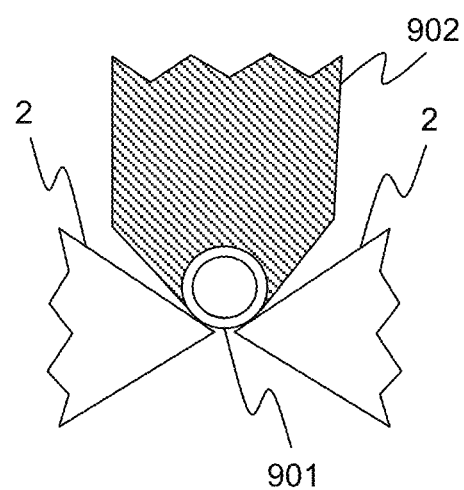
FIG. 9 shows a schematic cross-section of a conduit operatively coupled to a conduit holder and positioned in close proximity to the apex edges of the magnetic field guides in a magnetic separation device, according to embodiments of the present disclosure.

FIG. 9 shows a schematic cross-section of a conduit positioned in a magnetic separation device. Fluid sample flows through conduit 901, which is operatively coupled to a conduit holder 902 and positioned in a magnetic separation device and in close proximity to the apex edges of the magnetic field guides 2. The conduit 901 is a tubing, which can be flexible or rigid, and is positioned with its outside surface in contact with the magnetic field guides 2, but not between the apex edges of the magnetic field guides, as shown in FIG. 9. Conduit holder 902 facilitates positioning the conduit 901 in the magnetic separation device such that a longitudinal axis of the conduit 901 is substantially parallel to the longitudinal axes of the magnetic field guides 2.

Figures 10A, 10B:
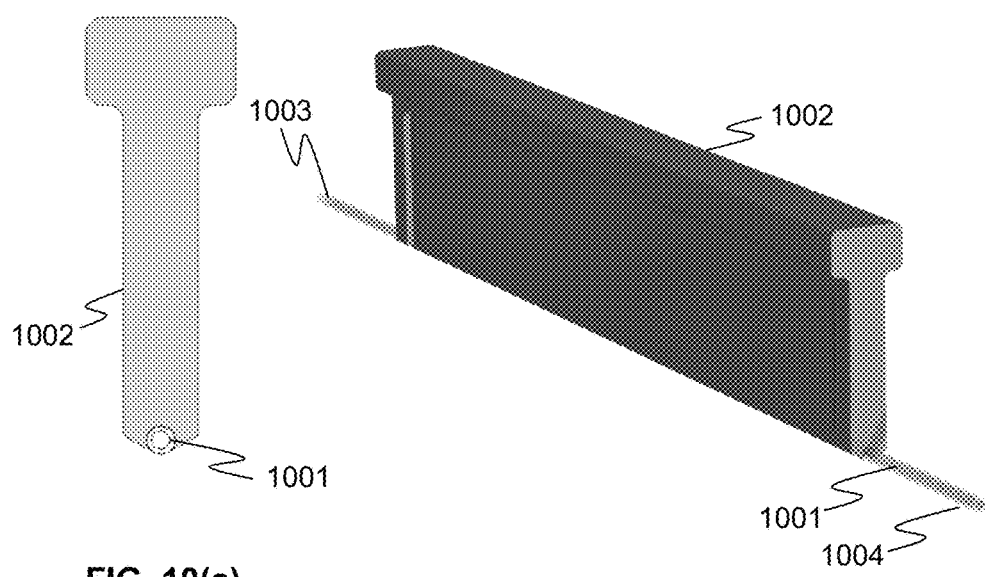
FIG. 10(a) shows a schematic of a front view of a conduit operatively coupled to a conduit holder, according to embodiments of the present disclosure.
FIG. 10(b) shows a schematic of a three-dimensional perspective view of a conduit operatively coupled to a conduit holder, according to embodiments of the present disclosure.

FIG. 10(a) is a front view of a conduit 1001 operatively coupled to a conduit holder 1002. FIG. 10(b) is a three-dimensional schematic of the conduit 1001 operatively coupled to the conduit holder 1002. The conduit 1001 has a central flow path that carries the flow of the sample fluid through the magnetic separation device. The conduit 1001 also includes also includes two openings 1003 and 1004, which may be connected to a fluid reservoir, a fluid transfer connector or an adapter, as desired.

Figure 11:
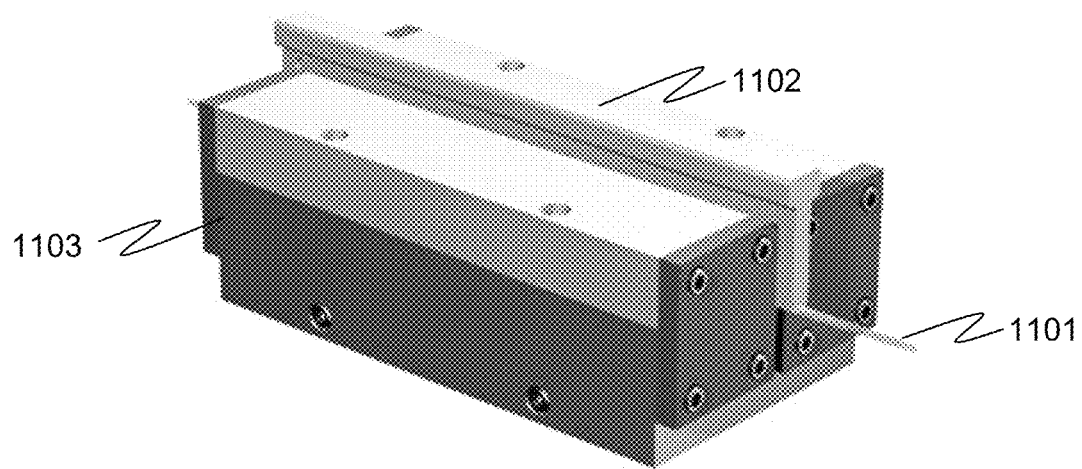
FIG. 11 shows a three-dimensional perspective view of a conduit operatively coupled to a conduit holder and positioned in a magnetic separation device, according to embodiments of the present disclosure.

FIG. 11 is a three-dimensional perspective view of the conduit 1101 operatively coupled to a conduit holder 1102 positioned in a magnetic separation device 1103. The conduit 1101 is positioned above the gap between the opposing apex edges of the magnetic field guides as shown in FIG. 9. A liquid sample with magnetically labeled biological or chemical moieties flows within the conduit 1101 and adjacent the tapered apex edges of the magnetic field guides. The magnetic field and magnetic field gradient produced by the magnetic field sources attracts the magnetic labels and magnetically labeled moieties in the flowing sample. The magnetic labels and magnetically labeled components are then pulled to and retained at the inner surface of the conduit proximal to the apex edges of the magnetic field guides. Thus, magnetic labels and magnetically labeled moieties are separated from the flowing solution and retained within the conduit. After the sample solution is flowed through the conduit and a plurality of magnetic labels and magnetically labeled moieties are separated from the flowing solution, the conduit is then positioned away from the magnetic field guides and the magnetic field within the conduit becomes approximately zero. By flushing the retained magnetic labels and magnetically labeled moieties from the conduit with a solution (e.g., a buffer solution), the magnetic labels and magnetically labeled moieties can be recovered from the conduit.

Magnetic Labels

Magnetic labels are labeling moieties that are retained by the device for separating magnetically labeled moieties in a sample. Magnetic labels of interest may be retained by the device if they flow through a portion of a conduit in close proximity to the magnetic field produced by the device, e.g., between the magnetic field sources and/or between the magnetic field guides of the device).

Magnetic labels useful in the practice of certain embodiments of the present disclosure are magnetic particles, such as, but not limited to ferromagnetic, paramagnetic, superparamagnetic, anti-ferromagnetic, or ferrimagnetic particles. In certain instances, the magnetic particles appear "nonmagnetic" (e.g., have a remnant magnetization of substantially zero) in the absence of a magnetic field. Magnetic particles with a substantially zero remnant magnetization may not substantially agglomerate with each other in solution in the absence of an external magnetic field.

The magnetic particles may be chemically stable in a biological environment, which may facilitate their use in the assay conditions. In some cases, the magnetic particles are biocompatible, e.g., water soluble and functionalized so that they may be readily attached to biomolecules of interest, such as an antibody that specifically binds to a target analyte. By associating or binding magnetic particles to a specific antibody, the magnetic particles may be targeted to a specific analyte through the specific binding interactions between the antibody and complementary antigen. In some instances, the magnetic label may be bound to the protein or antibody as described above through a non-covalent or a covalent bond with each other. Examples of non-covalent associations include non-specific adsorption, binding based on electrostatic (e.g., ion, ion pair interactions), hydrophobic interactions, hydrogen bonding interactions, specific binding through a specific binding pair member covalently attached to the surface of the magnetic particle, and the like. Examples of covalent binding include covalent bonds formed between the biomolecule and a functional group present on the surface of the magnetic particle, e.g. —OH, where the functional group may be naturally occurring or present as a member of an introduced linking group.

In certain embodiments, the magnetic particles are nanoparticles. By "nanoparticle" is meant a particle having an average size (e.g., mean diameter) in the range of 1 nm to 1000 nm. In certain embodiments, the average size (e.g., mean diameter) of the magnetic nanoparticles is sub-micron sized, e.g., from 1 nm to 1000 nm, or from 1 nm to 500 nm, or from 5 nm to 250 nm, such as from 5 nm to 150 nm, including from 5 nm to 50 nm. For example, magnetic nanoparticles having a mean diameter of 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, 150 nm, and 200 nm as well as nanoparticles having mean diameters in ranges between any two of these values, are suitable for use herein. In certain embodiments, the magnetic particles are substantially uniform in shape. For example, the magnetic particles may be spherical in shape. In addition to a spherical shape, magnetic nanoparticles suitable for use herein can be shaped as disks, rods, coils, fibers, pyramids, and the like.

Methods

Aspects of the present disclosure include methods of separating magnetically labeled moieties in a sample. The magnetically labeled moieties may be separated from the other components of the sample, such as non-magnetically labeled moieties (e.g., moieties that are not associated with a magnetic label).

In certain embodiments, the method includes positioning a conduit in a magnetic separation device as described above. The positioning may be performed manually or automatically. In embodiments where the positioning is performed manually, the user may position the conduit in the device such that the conduit is aligned proximal to (e.g., adjacent to or between) the magnetic field guides of the device. For instance, positioning the conduit may include aligning the conduit such that a longitudinal axis of the conduit is substantially parallel to a longitudinal axis of the magnetic field guides (e.g., the longitudinal axis of the first magnetic field guide and the longitudinal axis of the second magnetic field guide). In embodiments where the positioning is performed automatically by the device, the device may be programmed to position the conduit proximal to (e.g., adjacent to or between) the magnetic field guides without the intervention of the user. For example, the device may automatically align the conduit such that the longitudinal axis of the conduit is substantially parallel to the longitudinal axis of the magnetic field guides (e.g., the longitudinal axis of the first magnetic field guide and the longitudinal axis of the second magnetic field guide).

Aspects of the method further include applying a magnetic field to the sample. In some instances, the sample is a sample solution flowing through the conduit, thus the method includes applying a magnetic field to the sample flowing through the conduit. In certain instances, the method includes applying a magnetic field having a magnetic flux sufficient to separate magnetically labeled moieties from non-magnetically labeled moieties in the sample. The magnetic field may be applied continuously as the sample flows through the conduit, or may be applied discontinuously in a pulsed application. In certain embodiments, the magnetic field source is a permanent magnet as described above, and thus the magnetic field is applied continuously to the sample as the sample flows through the conduit.

In certain embodiments, the method includes positioning the conduit away from the magnetic field. The conduit may be positioned away from the magnetic field such that the applied external field on the conduit is substantially zero. Positioning the conduit away from the magnetic field may be achieved by removing the conduit from the device. For instance, the conduit may be removed from its position proximal to (e.g., adjacent to or between) the magnetic field guides and moved to a position away from the magnetic field source and the magnetic field guides. Positioning the conduit away from the magnetic field may facilitate the subsequent recovery of any magnetically labeled moieties that were retained in the conduit during the assay. In certain instances, positioning the conduit away from the magnetic field may be performed manually, while in other embodiments, positioning the conduit away from the magnetic field may be performed automatically (e.g., without the intervention of the user).

In some instances, positioning the conduit away from the magnetic field may be achieved by moving the magnetic field source (and the associated magnetic field guides) away from the conduit. For example, in embodiments that include one magnetic field source, the magnetic field source and the associated magnetic field guides may be moved to a position away from the conduit such that the magnetic field guides do not produce a magnetic field having sufficient magnetic field strength, gradient strength, and/or magnetic flux to retain the magnetically labeled moieties in the conduit.

In embodiments that include two magnetic field sources, the first magnetic field source and the second magnetic field source may be moved to positions away from the conduit. The magnetic field sources may be moved such that the distance between the magnetic field sources is greater than the distance between the magnetic field sources during the assay. For instance, the magnetic field sources may be moved to positions away from the conduit such that the distance between the apex edges of the magnetic field guides is greater than the distance between the apex edges of the magnetic field guides during the assay. In some cases, the magnetic field sources may be moved to positions away from the conduit such that the magnetic field guides do not produce a magnetic field having sufficient magnetic field strength, gradient strength, and/or magnetic flux to retain the magnetically labeled moieties in the conduit.

Positioning the conduit away from the magnetic field may facilitate the subsequent recovery of any magnetically labeled moieties that were retained in the conduit during the assay. For example, after positioning the conduit away from the magnetic field, the magnetically labeled moieties retained in the conduit may be recovered by flushing the magnetically labeled moieties from the conduit. For instance, the magnetically labeled moieties may be recovered by flowing a buffer or other compatible solution through the conduit to flush (e.g., wash) the magnetically labeled moieties from the conduit. Alternatively, the magnetically labeled moieties may be recovered from the conduit by centrifugation, application of a vacuum, pumping, combinations thereof, and the like.

Aspects of the methods disclosed herein may further include concentrating the recovered magnetically labeled moieties. After performing the magnetic separation assay as described herein, the magnetically labeled moieties that were retained in the conduit during the magnetic separation assay may be recovered from the conduit by flushing the magnetically labeled moieties from the conduit as described above. In certain embodiments, it may be desirable to increase the concentration of the magnetically labeled moieties in the solution that is flushed from the conduit. Thus, the method may include concentrating (e.g., increasing the concentration of) the magnetically labeled moieties in the solution that was flushed from the conduit. Concentrating the magnetically labeled moieties may include passing the solution that was flushed from the conduit that contains the magnetically labeled moieties through a concentration device. For example, the concentration device may include, but is not limited to, an acoustic concentrator. Further description of acoustic concentrators is found in U.S. Pat. No. 6,929,750, the disclosure of which is hereby incorporated by reference.

Assay methods disclosed herein may be qualitative or quantitative. Thus, as used herein, the term "detection" or "separation" refers to both qualitative and quantitative determinations, and therefore includes "measuring" and "determining a level" of magnetically labeled moieties in a sample.

Aspects of the methods disclosed herein may further include attaching a magnetic label to one or more target moieties in a sample prior to performing the magnetic separation assay (e.g., prior to applying the magnetic field to the sample). As such, the method may include magnetically labeling one or more moieties in a sample prior to performing the magnetic separation assay. The magnetic label may be stably associated with the moiety (or moieties) of interest through non-covalent or covalent interactions as described above. For example, the magnetic label may be associated with the moiety of interest through a binding interaction between a binding pair of molecules.

The binding pair of molecules may vary depending on the binding interaction of interest. Binding interactions of interest include any interaction between the binding pair of molecules, where the binding interaction occurs with specificity between the binding pair of molecules under the environmental conditions of the binding interaction. Examples of binding interactions of interest include, but are not limited to: nucleic acid hybridization interactions, protein-protein interactions, protein-nucleic acid interactions, enzyme-substrate interactions and receptor-ligand interactions, e.g., antibody-antigen interactions and receptor-agonist or antagonist interactions.

Examples of molecules that have molecular binding interactions of interest include, but are not limited to: biopolymers and small molecules, which may be organic or inorganic small molecules. A "biopolymer" is a polymer of one or more types of repeating units. Biopolymers may be found in biological systems (although they may be made synthetically) and may include peptides, polynucleotides, and polysaccharides, as well as such compounds composed of or containing amino acid analogs or non-amino acid groups, or nucleotide analogs or non-nucleotide groups. As such, biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. For example, a "biopolymer" may include DNA (including cDNA), RNA, oligonucleotides, PNA, other polynucleotides, and the like. A "biomonomer" references a single unit, which can be linked with the same or other biomonomers to form a biopolymer (e.g., a single amino acid or nucleotide with two linking groups, one or both of which may have removable protecting groups).

In some instances, the binding pair of molecules are ligands and receptors, where a given receptor or ligand may or may not be a biopolymer. The term "ligand" as used herein refers to a moiety that is capable of covalently or otherwise chemically binding a compound of interest. Ligands may be naturally-occurring or manmade. Examples of ligands include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, proteins, and the like. The term "receptor" as used herein is a moiety that has an affinity for a ligand. Receptors may be attached, covalently or non-covalently, to a binding member, either directly or via a specific binding substance. Examples of receptors include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, organelles, and the like. A "ligand receptor pair" is formed when two molecules have combined through molecular recognition to form a complex.

Accordingly, the methods may include detecting a binding interaction between a binding pair of molecules. The binding interaction may include one member of the binding pair of molecules that is labeled with a magnetic label as described herein. For example, one member of the binding pair of molecules may be magnetically labeled and may bind to its complementary binding pair member to form a binding pair complex. The binding pair complex may be separated from the moieties not of interest in the sample using a magnetic separation device and methods as described herein. After performing the magnetic separation assay, the binding pair complex may be detected using any convenient method, such as, but not limited to, flow cytometry, fluorescence detection, high-performance liquid chromatography (HPLC), electrophoresis, combinations thereof, and the like.

Aspects of methods of the present disclosure may further include analyzing the separated magnetically labeled moieties. In certain instances, the magnetically labeled moieties are analyzed subsequent to being separated from the non-magnetically labeled moieties in the sample, as described above. As such, the method may include analyzing the magnetically labeled moieties in the eluent from the magnetic separation device. In certain embodiments, the method includes analyzing the magnetically labeled moieties to determine information about the magnetically labeled moieties. For example, analyzing the magnetically labeled moieties may include counting the number of magnetically labeled moieties that were retained by the magnetic separation device. In some instances, the analyzing includes sorting the magnetically labeled moieties. For instance, the method may include counting and/or sorting the magnetically labeled moieties using a flow cytometry device. In certain cases, analyzing the magnetically labeled moieties includes determining one or more physical and/or chemical properties of the magnetically labeled moieties, such as, but not limited to, fluorescence, mass, charge, chemical composition, UV absorption, infrared absorption, light scattering, combinations thereof, and the like.

Systems

Systems according to embodiments of the present disclosure include one or more magnetic separation devices for separating magnetically labeled moieties in a sample. Each of the one or more magnetic separation devices may be configured as described according to the present disclosure. For instance, the magnetic separation device includes a magnetic field source, a first magnetic field guide, and a second magnetic field guide as described herein. In addition, the system includes a conduit positioned proximal to the first magnetic field guide and the second magnetic field guide.

In certain embodiments, the system includes more than one magnetic separation device. For instance, the system may include 2 or more magnetic separation devices, such as 3 or more, or 4 or more, or 5 or more, or 6 or more, or 7 or more, or 8 or more, or 9 or more, or 10 or more magnetic separation devices. The magnetic separation devices may be arranged in series such that the magnetic separation devices are positioned upstream and downstream from each other in series. Arranging the magnetic separation devices in series may facilitate the progressive separation of magnetically labeled moieties from the same sample. In some instances, the magnetic separation devices are arranged in parallel. Arranging the magnetic separation devices in parallel may facilitate the simultaneous separation of magnetically labeled moieties from a plurality of samples. In certain cases, the magnetic separation devices are arranged in series and in parallel.

In certain embodiments, the system includes more than one magnetic separation device, for example two magnetic separation devices (e.g., a first magnetic separation device and a second magnetic separation device). The first and second magnetic separation devices may be arranged in series as described above. In some instances, the devices may be configured such that the apex edges of the first and second magnetic field guides of the first magnetic separation device have substantially the same profiles as the apex edges of the first and second magnetic field guides of the second magnetic separation device. For example, the apex edges of the first and second magnetic field guides of the first magnetic separation device and the apex edges of the first and second magnetic field guides of the second magnetic separation device may each have a linear profile (or any other profile as desired, as described above). In other embodiments, the devices may be configured such that the apex edges of the first and second magnetic field guides of the first magnetic separation device have different profiles from the apex edges of the first and second magnetic field guides of the second magnetic separation device. For example, the apex edges of the first and second magnetic field guides of the first magnetic separation device may each have a linear profile, and the apex edges of the first and second magnetic field guides of the second magnetic separation device may each have a saw-tooth profile. The above examples are for illustrative purposes, and other combinations of profiles for the apex edges of the magnetic separation devices are also possible.

Embodiments of systems of the present disclosure may also include a concentrator (e.g., a particle concentration device). The concentrator may be arranged downstream from the magnetic separation device. In some instances, the concentrator is configured to increase the concentration of magnetically labeled moieties in the eluent from the magnetic concentration device. The concentrator may be any type of concentrator, and in some embodiments is an acoustic concentrator.

Aspects of systems of the present disclosure may also include a particle analysis device. The particle analysis device may be arranged downstream from the magnetic separation device, and in certain instances may be arranged downstream from the concentrator. The particle analysis device may be configured to analyze the magnetically labeled moieties and determine information about the magnetically labeled moieties. For example, the particle analysis device may be configured to count the number of magnetically labeled moieties that were retained by the magnetic separation device. In some instances, the particle analysis device may be configured to sort the magnetically labeled moieties. In certain cases, the particle analysis device may analyze the magnetically labeled moieties to determine one or more physical and/or chemical properties of the magnetically labeled moieties, such as, but not limited to, fluorescence, mass, charge, chemical composition, UV absorption, infrared absorption, light scattering, combinations thereof, and the like. In certain embodiments, the particle analysis device includes a flow cytometer, a mass spectrometer, an electrophoresis device, a high-performance liquid chromatography (HPLC) device, a UV spectrometer, an infrared spectrometer, and the like. In some instances, the particle analysis device is a flow cytometer.

Systems of the present disclosure may further include other support devices and/or additional components that may facilitate the performance of the magnetic separation assay and/or any subsequent analysis of the separated magnetically labeled moieties. For example, the system may further include a computer programmed to perform the magnetic separation assay, fluid handling components configured to provide a flow of the sample solution and/or buffer through the system (e.g., a pump, a vacuum source, a fluid reservoir, valves, inlets, outlets, etc.), components associated with the magnetic separation device (e.g., motors configured to position the magnetic field source and magnetic field guides), and other components as desired.

The systems may generally include one or more magnetic separation devices as described herein and a processor configured to control the one or more magnetic separation devices. These two components may be integrated into the same article of manufacture as a single unit, or distributed among two or more different units (e.g., as a system) where the two or more different units are in communication with each other, e.g., via a wired or wireless communication protocol.

Accordingly, aspects of the present disclosure further include systems, e.g., computer based systems, which are configured to separate magnetically labeled moieties in a sample as described above. A "computer-based system" refers to the hardware, software, and data storage devices used to analyze the information of the present invention. The minimum hardware of embodiments of the computer-based systems includes a central processing unit (CPU) (e.g., a processor), an input device, an output device, and data storage device. Any one of the currently available computer-based systems may be suitable for use in the embodiments disclosed herein. The data storage device may include any manufacture including a recording of the present information as described above, or a memory access means that can access such a manufacture. For example, embodiments of the subject systems may include the following components: (a) a communications module for facilitating information transfer between the system and one or more users, e.g., via a user computer or workstation; and (b) a processing module for performing one or more tasks involved in the analysis of the magnetically labeled moieties.

In addition to the magnetic separation device, systems of the present disclosure may include a number of additional components, such as data output devices, e.g., monitors, printers, and/or speakers, data input devices, e.g., interface ports, a keyboard, a mouse, etc., fluid handling components, power sources, etc.

Utility

The subject devices, methods, systems and kits find use in a variety of different applications where it is desirable to separate magnetically labeled moieties from non-magnetically labeled moieties in a sample. For example, the subject devices, methods, systems and kits find use in detecting the presence of a moiety of interest in a sample. The moiety of interest may be magnetically labeled and then separated from non-magnetically labeled moieties (e.g., by being retained in the conduit while non-magnetically labeled moieties flow through the conduit) by using the devices, methods, systems and kits described herein. In other embodiments, the moiety of interest is not magnetically labeled and other moieties that are not of interest in the sample are magnetically labeled. In these embodiments, the non-magnetically labeled moieties of interest are not retained by the device and flow through the conduit, where they may be collected and/or further analyzed. The magnetically labeled moieties that are not of interest are retained in the conduit and thus separated from the non-magnetically labeled moieties of interest.

In certain embodiments, the subject devices, methods, systems and kits find use in detecting a binding interaction of interest. In certain embodiments, the binding interaction is a binding interaction, such as, but not limited to, nucleic acid hybridization, a protein-protein interaction, a receptor-ligand interaction, an enzyme-substrate interaction, a protein-nucleic acid interaction, and the like. In some instances, the subject methods, systems and kits find use in drug development protocols where the detecting a molecular binding interaction may be desired. For example, drug development protocols may use the subject devices, methods, systems and kits to detect molecular the binding interactions between antibodies and antigens, or hybridization interactions between nucleic acids, or binding interactions between proteins, or binding interactions between receptors and ligands, or binding interactions between enzymes and substrates, or binding interactions between proteins and nucleic acids, and the like. For instance, detecting binding interactions such as these may facilitate the development of antibody-based drugs.

The subject devices, methods, systems and kits also find use in detecting molecular binding interactions between binding pairs that are included in complex samples. In some instances, the complex samples may be analyzed directly without separating the binding molecules of interest from the other proteins or molecules that are not of interest that are in the sample. In certain cases, proteins or molecules that are not of interest are not bound by the magnetic labels and are not retained in the conduit of the magnetic separation device. Thus, the subject devices, methods, systems and kits find use in assay protocols where complex samples may be used and where the binding interactions of interest may be detected with no purification of the sample necessary for detection of the binding interactions of interest.

Kits

Also provided are kits for practicing one or more embodiments of the above-described methods and/or for use with embodiments of the devices and systems described above. The subject kits may vary, and may include various components and reagents. Reagents and components of interest include those mentioned herein with respect to magnetic separation devices or components thereof, and include, but are not limited to, magnetic labels (e.g., magnetic nanoparticles), binding agents, buffers, fluid flow conduits (e.g., disposable fluid flow conduits), etc.

In some instances, the kits include at least reagents finding use in the methods (e.g., as described above); and a computer readable medium having a computer program stored thereon, wherein the computer program, when loaded into a computer, operates the computer to perform a magnetic separation assay as described herein; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Blu-Ray, computer readable memory device (e.g., hard drive or flash memory), etc., on which the information has been recorded. Yet another means that may be present is a website address which may be used via the Internet to access the information at a removed site. Any convenient means may be present in the kits.

The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Experiments were performed using a device for separating magnetically labeled moieties in a sample, according to embodiments of the present disclosure.

Materials and Methods

Magnetic Separation Device

The magnetic separation device included six permanent magnets (N45 rare earth Neodymium (NdFeB) bar magnet, 2 in.×0.5 in.×0.5 in., CMS Magnetics, Inc.) and six wedge-shaped magnetic field guides. The magnetic field guides were made of stainless steel and had a 60 degree apex angle. The apex edges of each magnetic field guides had linear profiles. The six permanent magnets were arranged into two sets of three magnets. Each set of three magnets had overall dimensions of 6 in.×0.5 in.×0.5 in. The first and second sets of magnets were positioned directly opposite from each other in the device. Each permanent magnet had a corresponding magnetic field guide attached, and the apex edges of the first set of magnetic field guides were directly opposite and parallel to the apex edges of the second set of magnetic field guides. During the separation assay, the gap between the apex edges of the two sets of magnetic field guides was 1 mm. The magnetic flux density in the gap between the apex edges of the magnetic field guides was measured to be 1.1 Tesla and the magnetic field gradient was 0.8 T/mm. The magnetic flux was localized in the gap between the apex edges of the magnetic field guides with a direction going from the first set of magnets to the second set of magnets.

Conduit

The conduit was silicone tubing with a 3 mm outer diameter and a 2 mm inner diameter. The effective length of the conduit was 6 inches, which corresponds to the length of the set of magnets in contact with the conduit.

Reagents and Sample for Separating Magnetically Labeled Moieties in a Sample

BD Imag™ Human CD4 T Lymphocyte Enrichment Set (Becton, Dickinson and Co.) that included biotin human CD4 T lymphocyte enrichment assay mixture and streptavidin coated magnetic particles was used in the experiments. The magnetic particles were superparamagnetic particles having an average diameter ranging from 200 nm to 400 nm and a stock concentration of 200 µg/ml. According to the manufacturer's recommended protocol, 5 µl of the cocktail was used per million cells. After incubation and washing, 5 µl streptavidin coated magnetic particles was used per million cells. The experimental sample was human peripheral blood mononuclear cells (PBMCs) prepared by using BD Vacutainer® CPT™ Cell Preparation Tube with Sodium Citrate (Becton, Dickinson and Co.). The PBMCs were suspended in 1× phosphate buffered saline (PBS) with 0.5% bovine serum albumin (BSA) and 20 mM EDTA in a concentration of 2 to 50 million cells per ml. Biotinylated antibodies in the assay mixture bound to all populations in PBMCs except CD4+ T lymphocytes. Streptavidin that was conjugated to magnetic particles in the assay mixture bound to biotin specifically. With the above two step binding method, all cells in PBMCs except CD4+ T lymphocytes were magnetically labeled by the specific binding interaction between the biotin labeled PBMCs and the streptavidin coated magnetic particles.

The sample was flowed through the conduit positioned in between the magnetic field guides in a magnetic separation device and magnetically labeled cells were captured in the magnetic field in the gap between the apex edges of the magnetic field guides. The CD4+ T lymphocytes, which were not magnetically labeled, were not retained in the conduit and passed through the conduit to a detector or collection tube positioned downstream from the magnets. When the separation was finished, the conduit was removed from between the magnetic field guides and the captured cells were flushed out with buffer under higher pressure. Because human T regulatory cells are a small subpopulation of CD4+ T lymphocytes, magnetic depletion of non CD4+ T lymphocytes is a way to enrich T regulatory cells in a sample.

Operation Conditions

Magnetically labeled cells and non-labeled cells passed through the magnetic separation device in a conduit driven by a peristaltic pump or air pressure. The flow rate was 200 µl/min to 400 µl/min. For example, an air compressor was used to apply 18 psi to the sample in the conduit to achieve a 400 µl/min flow rate in the conduit. With 2 to 50 million PBMCs in 1 ml sample volume, the separation and recovery was completed in 10 minutes or less. The experiment was performed at room temperature. Optionally, the labeled PBMCs were kept on ice before performing the separation assay.

Results

Both magnetically captured cells and non-captured cells were analyzed with a flow cytometer after fluorescent staining. The results indicated that the magnetic separation device had a 98% separation efficiency and 90% of the T regulatory cells were recovered.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A device for separating magnetically labeled moieties in a sample, the device comprising:
    a first magnetic field source;
    magnetic field guides consisting of:
        a first magnetic field guide having a wedge-shaped portion with a single apex edge and
        a second magnetic field guide having a wedge-shaped portion with a single apex edge; and
    a conduit consisting of a single linear flow channel having a longitudinal axis that is parallel to a longitudinal axis of the first magnetic field guide and a longitudinal axis of the second magnetic field guide,
    wherein one or more of the first and second magnetic field guides is configured to increase a magnetic flux from the magnetic field source, the single apex edges of the first and second magnetic field guides are aligned substantially across from and parallel to each other, and the device is configured to separate magnetically labeled moieties from non-magnetically labeled moieties in the sample.

2. The device of claim 1, wherein the first and second magnetic field guides have cross-sectional profiles that taper to a point or are rounded at their apex edges.

3. The device of claim 1, wherein the apex edges of the first and second magnetic field guides each have a linear profile.

4. The device of claim 1, wherein the first and second magnetic field guides each comprise a soft magnet, and the magnetic field source comprises a permanent magnet.

5. The device of claim 1, further comprising a second magnetic field source, wherein the first magnetic field guide is disposed on a surface of the magnetic field source facing the second magnetic field guide and is configured to increase the magnetic flux from the magnetic field source, and the second magnetic field guide is disposed on a surface of the second magnetic field source facing the first magnetic field guide is configured to increase a magnetic flux from the second magnetic field source.

6. The device according to claim 1, wherein the conduit is positioned between the first and second magnetic field guides such that its central longitudinal axis is equidistant from the apex edges of the first and second magnetic field guides.

7. The device according to claim 1, wherein the conduit has a rectangular cross-sectional profile.

8. The device according to claim 1, wherein the conduit has a cross-sectional area upstream from the portion of the conduit positioned between the magnetic field guides that is greater than the cross-sectional area of the portion of the conduit positioned between the magnetic field guides.

9. The device according to claim 1, wherein the conduit is operatively coupled to a conduit holder.

10. The device according to claim 5, wherein the first magnetic field source and the second magnetic field source have magnetization vectors aligned in substantially the same direction.

* * * * *